(12) United States Patent
Wondka

(10) Patent No.: US 8,573,219 B2
(45) Date of Patent: *Nov. 5, 2013

(54) METHOD AND DEVICE FOR NON-INVASIVE VENTILATION WITH NASAL INTERFACE

(75) Inventor: Anthony D. Wondka, Thousand Oaks, CA (US)

(73) Assignee: Breathe Technologies, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,219

(22) Filed: Dec. 9, 2011

(65) Prior Publication Data

US 2012/0073576 A1 Mar. 29, 2012

Related U.S. Application Data

(60) Continuation of application No. 12/076,062, filed on Mar. 13, 2008, now Pat. No. 8,136,527, which is a division of application No. 10/922,054, filed on Aug. 18, 2004, now Pat. No. 7,406,966.

(60) Provisional application No. 60/495,812, filed on Aug. 18, 2003, provisional application No. 60/511,820, filed on Oct. 14, 2003.

(51) Int. Cl.
*A61M 15/08* (2006.01)
*A61M 15/00* (2006.01)
*A61M 16/06* (2006.01)
*A61M 16/00* (2006.01)

(52) U.S. Cl.
USPC ............ 128/207.18; 128/207.13; 128/206.21; 128/200.24

(58) Field of Classification Search
USPC ............ 128/200.24, 200.26, 206.21, 207.13, 128/207.14, 207.18; 604/174–180; 24/336, 24/339, 579, 575, 589, 669, 702; 403/389, 403/385, 397, 406.1, 340, 373, 314, 309, 403/364, 339, 331
See application file for complete search history.

(56) References Cited

U.S. PATENT DOCUMENTS 50,641 A 10/1865 Stone
428,592 A 5/1890 Chapman
(Continued)

FOREIGN PATENT DOCUMENTS

DE 19626924 1/1998
DE 29902267 U1 7/1999
(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Annette Dixon
(74) *Attorney, Agent, or Firm* — Stetina Brunda Garred & Brucker

(57) ABSTRACT

A nasal ventilation interface including a pair of tubes configured to deliver a ventilation gas. The tubes are attachable at a first end to a ventilation gas supply hose and engageable at a second end with a person's nostril. A coupler is configured to align the pair of tubes with the person's nostrils, wherein each tube has an absence of pneumatic interconnection with the other tube.

17 Claims, 16 Drawing Sheets

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Piá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |

(56) References Cited

U.S. PATENT DOCUMENTS

| | | | |
|---|---|---|---|
| 4,938,212 | A | 7/1990 | Snook et al. |
| 4,944,310 | A | 7/1990 | Sullivan |
| 4,967,743 | A | 11/1990 | Lambert |
| 4,971,049 | A | 11/1990 | Rotariu et al. |
| 4,982,735 | A | 1/1991 | Yagata et al. |
| 4,986,269 | A | 1/1991 | Hakkinen |
| 4,989,599 | A | 2/1991 | Carter |
| 4,990,157 | A | 2/1991 | Roberts et al. |
| 5,000,175 | A | 3/1991 | Pue |
| 5,002,050 | A | 3/1991 | McGinnis |
| 5,005,570 | A | 4/1991 | Perkins |
| 5,018,519 | A | 5/1991 | Brown |
| 5,022,394 | A | 6/1991 | Chmielinski |
| 5,024,219 | A | 6/1991 | Dietz |
| 5,025,805 | A * | 6/1991 | Nutter ............... 128/207.18 |
| 5,038,771 | A | 8/1991 | Dietz |
| 5,042,478 | A * | 8/1991 | Kopala et al. ............ 128/207.18 |
| 5,046,491 | A | 9/1991 | Derrick |
| 5,046,492 | A | 9/1991 | Stackhouse et al. |
| 5,048,515 | A | 9/1991 | Sanso |
| 5,048,516 | A | 9/1991 | Soderberg |
| 5,052,400 | A | 10/1991 | Dietz |
| 5,054,484 | A | 10/1991 | Hebeler, Jr. |
| 5,058,580 | A | 10/1991 | Hazard |
| 5,074,299 | A | 12/1991 | Dietz |
| 5,076,267 | A | 12/1991 | Pasternack |
| 5,090,408 | A | 2/1992 | Spofford et al. |
| 5,097,827 | A | 3/1992 | Izumi |
| 5,099,836 | A | 3/1992 | Rowland et al. |
| 5,099,837 | A | 3/1992 | Russel, Sr. et al. |
| 5,101,820 | A | 4/1992 | Christopher |
| 5,103,815 | A | 4/1992 | Siegel et al. |
| 5,105,807 | A | 4/1992 | Kahn et al. |
| 5,107,830 | A | 4/1992 | Younes |
| 5,107,831 | A | 4/1992 | Halpern et al. |
| 5,113,857 | A | 5/1992 | Dickerman et al. |
| 5,117,818 | A | 6/1992 | Palfy |
| 5,117,819 | A | 6/1992 | Servidio et al. |
| 5,127,400 | A | 7/1992 | DeVries et al. |
| 5,134,995 | A | 8/1992 | Gruenke et al. |
| 5,134,996 | A | 8/1992 | Bell |
| 5,140,045 | A | 8/1992 | Askanazi et al. |
| 5,148,802 | A | 9/1992 | Sanders et al. |
| 5,161,525 | A | 11/1992 | Kimm et al. |
| 5,165,397 | A | 11/1992 | Arp |
| 5,181,509 | A | 1/1993 | Spofford et al. |
| 5,184,610 | A | 2/1993 | Marten et al. |
| 5,186,167 | A | 2/1993 | Kolobow |
| 5,193,532 | A | 3/1993 | Moa et al. |
| 5,193,533 | A | 3/1993 | Body et al. |
| 5,199,424 | A | 4/1993 | Sullivan et al. |
| 5,211,170 | A | 5/1993 | Press |
| 5,217,008 | A | 6/1993 | Lindholm |
| 5,233,978 | A | 8/1993 | Callaway |
| 5,233,979 | A | 8/1993 | Strickland |
| 5,239,994 | A | 8/1993 | Atkins |
| 5,239,995 | A | 8/1993 | Estes et al. |
| 5,243,972 | A | 9/1993 | Huang |
| 5,245,995 | A | 9/1993 | Sullivan et al. |
| 5,255,675 | A | 10/1993 | Kolobow |
| 5,258,027 | A | 11/1993 | Berghaus |
| 5,269,296 | A | 12/1993 | Landis |
| 5,271,388 | A | 12/1993 | Whitwam et al. |
| 5,271,391 | A | 12/1993 | Graves |
| 5,275,159 | A | 1/1994 | Griebel |
| 5,279,288 | A | 1/1994 | Christopher |
| 5,287,852 | A | 2/1994 | Arkinstall |
| 5,303,698 | A | 4/1994 | Tobia et al. |
| 5,303,700 | A | 4/1994 | Weismann et al. |
| 5,318,019 | A | 6/1994 | Celaya |
| 5,331,995 | A | 7/1994 | Westfall et al. |
| 5,335,656 | A | 8/1994 | Bowe et al. |
| 5,339,809 | A | 8/1994 | Beck, Jr. et al. |
| 5,349,946 | A | 9/1994 | McComb |
| 5,368,017 | A | 11/1994 | Sorenson et al. |
| 5,370,112 | A | 12/1994 | Perkins |
| 5,373,842 | A | 12/1994 | Olsson et al. |
| 5,375,593 | A | 12/1994 | Press |
| 5,388,575 | A | 2/1995 | Taube |
| 5,394,870 | A | 3/1995 | Johansson |
| 5,398,676 | A | 3/1995 | Press et al. |
| 5,398,682 | A | 3/1995 | Lynn |
| 5,400,778 | A | 3/1995 | Jonson et al. |
| 5,419,314 | A | 5/1995 | Christopher |
| 5,438,979 | A | 8/1995 | Johnson, Jr. et al. |
| 5,438,980 | A | 8/1995 | Phillips |
| 5,443,075 | A | 8/1995 | Holscher |
| 5,460,174 | A | 10/1995 | Chang |
| 5,460,613 | A | 10/1995 | Ulrich et al. |
| 5,474,062 | A | 12/1995 | DeVires et al. |
| 5,477,852 | A * | 12/1995 | Landis et al. ............ 128/207.18 |
| 5,485,850 | A | 1/1996 | Dietz |
| 5,490,502 | A | 2/1996 | Rapoport et al. |
| 5,503,146 | A | 4/1996 | Froehlich et al. |
| 5,503,497 | A | 4/1996 | Dudley et al. |
| 5,507,282 | A | 4/1996 | Younes |
| 5,509,409 | A | 4/1996 | Weatherholt |
| 5,513,628 | A | 5/1996 | Coles et al. |
| 5,513,631 | A | 5/1996 | McWilliams |
| 5,513,635 | A | 5/1996 | Bedi |
| 5,522,382 | A | 6/1996 | Sullivan et al. |
| 5,526,806 | A | 6/1996 | Sansoni |
| 5,529,060 | A | 6/1996 | Salmon et al. |
| 5,533,506 | A | 7/1996 | Wood |
| 5,535,738 | A | 7/1996 | Estes et al. |
| 5,537,997 | A | 7/1996 | Mechlenburg et al. |
| 5,538,002 | A | 7/1996 | Boussignac et al. |
| 5,542,415 | A | 8/1996 | Brody |
| 5,546,935 | A | 8/1996 | Champeau |
| 5,549,106 | A | 8/1996 | Gruenke et al. |
| 5,551,419 | A | 9/1996 | Froehlich et al. |
| 5,558,086 | A | 9/1996 | Smith et al. |
| 5,564,416 | A | 10/1996 | Jones |
| 5,575,282 | A | 11/1996 | Knoch et al. |
| 5,582,164 | A | 12/1996 | Sanders |
| 5,593,143 | A | 1/1997 | Ferrarin |
| 5,595,174 | A | 1/1997 | Gwaltney |
| 5,598,837 | A | 2/1997 | Sirianne, Jr. et al. |
| 5,598,840 | A | 2/1997 | lund et al. |
| 5,603,315 | A | 2/1997 | Sasso, Jr. |
| 5,605,148 | A | 2/1997 | Jones |
| 5,626,131 | A | 5/1997 | Chua et al. |
| 5,632,269 | A | 5/1997 | Zdrojkowski |
| 5,636,630 | A | 6/1997 | Miller et al. |
| 5,645,053 | A | 7/1997 | Remmers et al. |
| 5,645,054 | A | 7/1997 | Cotner et al. |
| 5,647,351 | A | 7/1997 | Weismann et al. |
| 5,669,377 | A | 9/1997 | Fenn |
| 5,669,380 | A | 9/1997 | Garry et al. |
| 5,676,132 | A | 10/1997 | Tillotson et al. |
| 5,676,135 | A | 10/1997 | McClean |
| 5,682,878 | A | 11/1997 | Ogden |
| 5,682,881 | A | 11/1997 | Winthrop et al. |
| 5,687,713 | A | 11/1997 | Bahr et al. |
| 5,687,714 | A | 11/1997 | Kolobow et al. |
| 5,687,715 | A | 11/1997 | Landis et al. |
| 5,690,097 | A | 11/1997 | Howard et al. |
| 5,692,497 | A | 12/1997 | Schnitzer et al. |
| 5,697,364 | A | 12/1997 | Chua et al. |
| 5,704,345 | A | 1/1998 | Berthon-Jones |
| 5,711,296 | A | 1/1998 | Kolobow |
| 5,715,812 | A | 2/1998 | Deighan et al. |
| 5,715,815 | A | 2/1998 | Lorenzen et al. |
| 5,720,278 | A | 2/1998 | Lachmann et al. |
| 5,735,268 | A | 4/1998 | Chua et al. |
| 5,735,272 | A | 4/1998 | Dillon et al. |
| 5,740,796 | A | 4/1998 | Skog |
| 5,752,511 | A | 5/1998 | Simmons et al. |
| 5,762,638 | A | 6/1998 | Shikani et al. |
| 5,778,887 | A * | 7/1998 | Curtiss ............ 128/845 |
| 5,791,337 | A | 8/1998 | Coles et al. |
| 5,819,723 | A | 10/1998 | Joseph |
| 5,826,579 | A | 10/1998 | Remmers et al. |
| 5,845,636 | A | 12/1998 | Gruenke et al. |

(56) References Cited

U.S. PATENT DOCUMENTS

| | | | |
|---|---|---|---|
| 5,865,173 A | 2/1999 | Froehlich | |
| 5,865,174 A | 2/1999 | Kloeppel | |
| 5,881,723 A | 3/1999 | Wallace et al. | |
| 5,904,648 A | 5/1999 | Arndt et al. | |
| 5,906,204 A | 5/1999 | Beran et al. | |
| 5,911,756 A | 6/1999 | Debry | |
| 5,915,379 A | 6/1999 | Wallace et al. | |
| 5,915,381 A | 6/1999 | Nord | |
| 5,918,597 A | 7/1999 | Jones et al. | |
| 5,921,238 A | 7/1999 | Bourdon | |
| 5,921,942 A | 7/1999 | Remmers et al. | |
| 5,921,952 A | 7/1999 | Desmond, III et al. | |
| 5,927,276 A | 7/1999 | Rodriguez | |
| 5,928,189 A | 7/1999 | Phillips et al. | |
| 5,931,160 A | 8/1999 | Gilmore et al. | |
| 5,931,162 A | 8/1999 | Christian | |
| 5,937,853 A | 8/1999 | Strom | |
| 5,937,855 A | 8/1999 | Zdrojkowski et al. | |
| 5,938,118 A | 8/1999 | Cooper | |
| 5,954,050 A | 9/1999 | Christopher | |
| 5,957,136 A | 9/1999 | Magidson et al. | |
| 5,964,223 A | 10/1999 | Baran | |
| 5,967,143 A * | 10/1999 | Klappenberger | 128/207.29 |
| 5,975,077 A | 11/1999 | Hofstetter et al. | |
| 5,975,081 A | 11/1999 | Hood et al. | |
| 5,979,440 A | 11/1999 | Honkonen et al. | |
| 5,989,193 A | 11/1999 | Sullivan | |
| 6,000,396 A | 12/1999 | Melker et al. | |
| 6,019,101 A | 2/2000 | Cotner et al. | |
| 6,039,696 A | 3/2000 | Bell | |
| 6,050,260 A | 4/2000 | Daniell et al. | |
| 6,076,519 A | 6/2000 | Johnson | |
| 6,085,747 A | 7/2000 | Axe et al. | |
| 6,091,973 A | 7/2000 | Colla et al. | |
| 6,093,169 A | 7/2000 | Cardoso | |
| 6,105,575 A | 8/2000 | Estes et al. | |
| 6,109,264 A | 8/2000 | Sauer | |
| 6,112,746 A | 9/2000 | Kwok et al. | |
| 6,119,694 A | 9/2000 | Correa et al. | |
| 6,120,460 A | 9/2000 | Abreu | |
| 6,123,668 A | 9/2000 | Abreu | |
| 6,131,571 A | 10/2000 | Lampotang et al. | |
| 6,135,970 A | 10/2000 | Kadhiresan et al. | |
| 6,152,132 A | 11/2000 | Psaros | |
| 6,152,134 A | 11/2000 | Webber et al. | |
| 6,158,432 A | 12/2000 | Biondi et al. | |
| 6,192,883 B1 | 2/2001 | Miller, Jr. | |
| 6,203,502 B1 | 3/2001 | Hilgendorf et al. | |
| 6,213,119 B1 | 4/2001 | Brydon et al. | |
| 6,213,955 B1 | 4/2001 | Karakasoglu et al. | |
| 6,220,244 B1 | 4/2001 | McLaughlin | |
| 6,224,560 B1 | 5/2001 | Gazula et al. | |
| 6,227,200 B1 | 5/2001 | Crump et al. | |
| 6,247,470 B1 | 6/2001 | Ketchedjian | |
| 6,269,811 B1 | 8/2001 | Duff et al. | |
| 6,269,812 B1 | 8/2001 | Wallace et al. | |
| 6,273,859 B1 | 8/2001 | Remmers et al. | |
| 6,286,508 B1 | 9/2001 | Remmers et al. | |
| D449,376 S | 10/2001 | McDonald et al. | |
| D449,883 S | 10/2001 | McDonald et al. | |
| 6,298,850 B1 | 10/2001 | Argraves | |
| 6,305,374 B1 | 10/2001 | Zdrojkowski et al. | |
| 6,314,957 B1 | 11/2001 | Boissin et al. | |
| 6,315,739 B1 | 11/2001 | Merilainen et al. | |
| D451,598 S | 12/2001 | McDonald et al. | |
| 6,328,038 B1 | 12/2001 | Kessler et al. | |
| 6,328,753 B1 | 12/2001 | Zammit | |
| 6,332,463 B1 | 12/2001 | Farrugia et al. | |
| 6,345,619 B1 | 2/2002 | Finn | |
| 6,357,438 B1 | 3/2002 | Hansen | |
| 6,357,440 B1 | 3/2002 | Hansen et al. | |
| 6,360,741 B2 | 3/2002 | Truschel | |
| 6,360,745 B1 | 3/2002 | Wallace et al. | |
| 6,363,933 B1 | 4/2002 | Berthon-Jones | |
| 6,367,474 B1 | 4/2002 | Berthon-Jones et al. | |
| 6,369,838 B1 | 4/2002 | Wallace et al. | |
| 6,371,114 B1 | 4/2002 | Schmidt et al. | |
| 6,378,520 B1 | 4/2002 | Davenport | |
| 6,390,091 B1 | 5/2002 | Banner et al. | |
| 6,394,088 B1 | 5/2002 | Frye et al. | |
| 6,398,739 B1 | 6/2002 | Sullivan et al. | |
| 6,418,928 B1 | 7/2002 | Bordewick et al. | |
| 6,422,240 B1 | 7/2002 | Levitsky et al. | |
| 6,423,001 B1 | 7/2002 | Abreu | |
| 6,427,690 B1 | 8/2002 | McCombs et al. | |
| 6,431,172 B1 | 8/2002 | Bordewick | |
| 6,435,181 B1 * | 8/2002 | Jones et al. | 128/204.18 |
| 6,439,228 B1 | 8/2002 | Hete et al. | |
| 6,439,229 B1 | 8/2002 | Du et al. | |
| 6,439,234 B1 | 8/2002 | Curti et al. | |
| 6,439,235 B1 | 8/2002 | Larquet et al. | |
| 6,450,164 B1 | 9/2002 | Banner et al. | |
| 6,450,166 B1 | 9/2002 | McDonald et al. | |
| 6,457,472 B1 | 10/2002 | Schwartz et al. | |
| 6,467,477 B1 | 10/2002 | Frank et al. | |
| 6,478,026 B1 | 11/2002 | Wood | |
| 6,494,202 B2 | 12/2002 | Farmer | |
| 6,494,206 B1 | 12/2002 | Bergamaschi et al. | |
| 6,505,623 B1 | 1/2003 | Hansen | |
| 6,505,624 B1 | 1/2003 | Campbell, Sr. | |
| 6,516,801 B2 | 2/2003 | Boussignac | |
| 6,520,176 B1 | 2/2003 | Dubois et al. | |
| 6,520,183 B2 | 2/2003 | Amar | |
| 6,530,373 B1 | 3/2003 | Patron et al. | |
| 6,532,958 B1 | 3/2003 | Buan et al. | |
| 6,532,960 B1 | 3/2003 | Yurko | |
| 6,536,432 B2 | 3/2003 | Truschel | |
| 6,536,436 B1 | 3/2003 | McGlothen | |
| 6,550,478 B2 | 4/2003 | Remmers et al. | |
| 6,553,992 B1 | 4/2003 | Berthon-Jones et al. | |
| 6,561,188 B1 | 5/2003 | Ellis | |
| 6,561,193 B1 | 5/2003 | Noble | |
| 6,564,797 B1 | 5/2003 | Mechlenburg et al. | |
| 6,564,800 B1 | 5/2003 | Olivares | |
| 6,568,391 B1 | 5/2003 | Tatarek et al. | |
| 6,571,794 B1 | 6/2003 | Hansen | |
| 6,571,796 B2 | 6/2003 | Banner et al. | |
| 6,571,798 B1 | 6/2003 | Thornton | |
| 6,575,159 B1 | 6/2003 | Frye et al. | |
| 6,575,944 B1 | 6/2003 | McNary et al. | |
| 6,584,973 B1 | 7/2003 | Biondi et al. | |
| 6,588,422 B1 | 7/2003 | Berthon-Jones et al. | |
| 6,588,423 B1 | 7/2003 | Sinderby | |
| 6,591,834 B1 | 7/2003 | Colla et al. | |
| 6,591,835 B1 | 7/2003 | Blanch | |
| 6,595,207 B1 | 7/2003 | McDonald et al. | |
| 6,595,215 B2 | 7/2003 | Wood | |
| 6,609,517 B1 | 8/2003 | Estes et al. | |
| 6,622,726 B1 | 9/2003 | Du | |
| 6,626,174 B1 | 9/2003 | Genger et al. | |
| 6,626,175 B2 | 9/2003 | Jafari et al. | |
| 6,629,525 B2 | 10/2003 | Hill et al. | |
| 6,629,527 B1 | 10/2003 | Estes et al. | |
| 6,629,529 B2 | 10/2003 | Arnott | |
| 6,631,919 B1 | 10/2003 | West et al. | |
| 6,634,356 B1 | 10/2003 | O'Dea et al. | |
| 6,635,021 B1 | 10/2003 | Sullivan et al. | |
| 6,640,806 B2 | 11/2003 | Yurko | |
| 6,644,305 B2 | 11/2003 | MacRae et al. | |
| 6,644,311 B1 | 11/2003 | Truitt et al. | |
| 6,644,315 B2 | 11/2003 | Ziaee | |
| 6,651,653 B1 | 11/2003 | Honkonen et al. | |
| 6,651,656 B2 | 11/2003 | Demers et al. | |
| 6,651,658 B1 | 11/2003 | Hill et al. | |
| 6,655,382 B1 | 12/2003 | Kolobow | |
| 6,655,385 B1 | 12/2003 | Curti et al. | |
| 6,666,208 B1 | 12/2003 | Schumacher et al. | |
| 6,668,828 B1 | 12/2003 | Figley et al. | |
| 6,668,829 B2 | 12/2003 | Biondi et al. | |
| 6,669,712 B1 | 12/2003 | Cardoso | |
| 6,675,796 B2 | 1/2004 | McDonald | |
| 6,675,801 B2 | 1/2004 | Wallace et al. | |
| 6,679,265 B2 * | 1/2004 | Strickland et al. | 128/207.18 |
| 6,681,764 B1 | 1/2004 | Honkonen et al. | |

(56) References Cited

U.S. PATENT DOCUMENTS

| | | |
|---|---|---|
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,187 B2 * | 2/2006 | Wood et al. ............... 128/206.11 |
| 6,997,881 B2 | 2/2006 | Green et al. |
| 7,000,612 B2 | 2/2006 | Jafari et al. |
| 7,000,613 B2 * | 2/2006 | Wood et al. ............... 128/206.11 |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 * | 6/2007 | Ruiz et al. ............... 128/207.11 |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,311,103 B2 * | 12/2007 | Jeppesen ............... 128/201.26 |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 * | 8/2008 | Wondka ............... 128/207.18 |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,472,707 B2 * | 1/2009 | Wood et al. ............... 128/207.18 |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |

(56) References Cited

U.S. PATENT DOCUMENTS

| | | |
|---|---|---|
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |

(56) References Cited

U.S. PATENT DOCUMENTS

| | | |
|---|---|---|
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratham et al. |
| 2008/0092905 A1 | 4/2008 | Gunaratham et al. |
| 2008/0092906 A1 | 4/2008 | Gunaratham et al. |
| 2008/0099024 A1 | 5/2008 | Gunaratham et al. |
| 2008/0099027 A1 | 5/2008 | Gunaratnam et al. |
| 2008/0105264 A1 | 5/2008 | Gunaratham et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |

(56) References Cited

U.S. PATENT DOCUMENTS

| | | | |
|---|---|---|---|
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO 2010/021556 | 2/2010 |
| WO | WO-2010/022363 | 2/2010 |
| WO | WO-2010/039989 | 4/2010 |
| WO | WO 2010/041966 | 4/2010 |
| WO | WO-2010/044034 | 4/2010 |
| WO | WO-2010/057268 | 5/2010 |
| WO | WO 2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |

(56) References Cited

FOREIGN PATENT DOCUMENTS

| WO | WO-2010/115169 | 10/2010 |
|---|---|---|
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO 2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO 2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiners Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiners Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiners Interview Summary in re: U.S. Appl. No. 11/523,519, dated Jan. 16, 2009, 10 pages.
In the U.S. Patent and Trademark Office, Examiners Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiners Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiners Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiners Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pp.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.

(56) References Cited

OTHER PUBLICATIONS

Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," *Respirology*, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Diaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.

MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.

(56) References Cited

OTHER PUBLICATIONS

Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.

\* cited by examiner

A-A

B-B

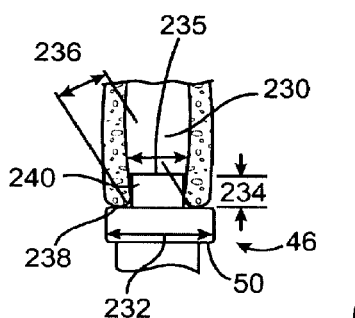
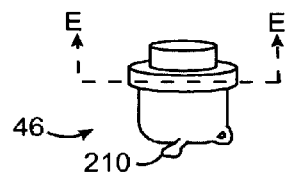
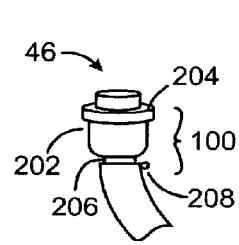
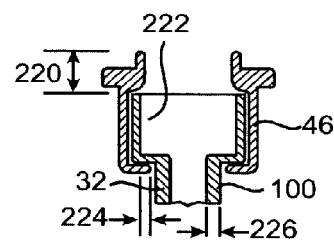
FIG. 14C  FIG. 14D  FIG. 14B  FIG. 14A  FIG. 14E
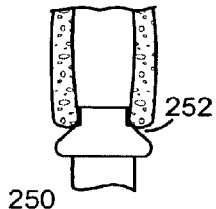 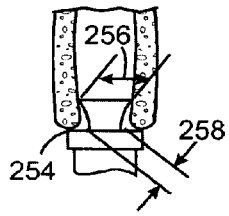 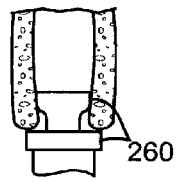 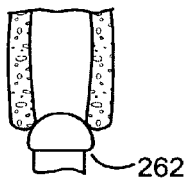
FIG. 15A  FIG. 15B  FIG. 15C  FIG. 15D
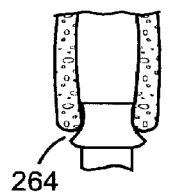 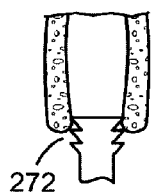 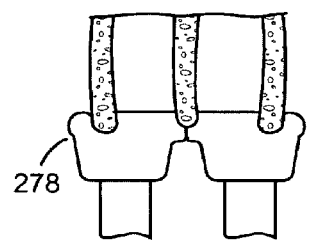
FIG. 15E  FIG. 15F  FIG. 15G
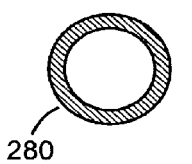 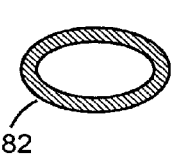 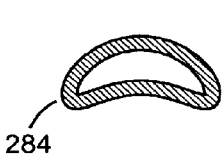 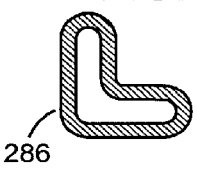 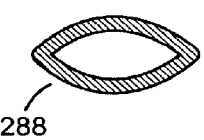
FIG.16A  FIG.16B  FIG.16C  FIG.16D  FIG.16E Section F-F

METHOD AND DEVICE FOR NON-INVASIVE VENTILATION WITH NASAL INTERFACE

CROSS REFERENCE TO RELATED APPLICATIONS

This application is a continuation of U.S. application Ser. No. 12/076,062, filed Mar. 13, 2008, now U.S. Pat. No. 8,136,527, which is a divisional application of U.S. application Ser. No. 10/922,054, filed Aug. 18, 2004, now U.S. Pat. No. 7,406,966, which claims priority to U.S. Provisional Patent Application No. 60/495,812 filed Aug. 18, 2003, and U.S. Provisional Patent Application No. 60/511,820 filed Oct. 14, 2003, the contents of which are incorporated herein in their entirety.

FIELD OF INVENTION

This invention relates to a non-invasive ventilation (NIV) patient interface device which provides a route of air entry into a patient's airway and lung. More particularly, this invention can be applied to Obstructive Sleep Apnea (OSA), a condition where the upper airway obstructs, however the teachings herein are applicable to other respiratory conditions.

BACKGROUND OF THE INVENTION

Non-invasive patient interface devices are used in a variety of medical procedures, such as emergency ventilation, anesthesia delivery and recovery, aerosolized medication delivery, augmentation of natural breathing, supplemental oxygen delivery, mechanical ventilation, weaning from mechanical ventilation and for treating Obstructive Sleep Apnea. In the later case continuous positive airway pressure (CPAP) or continuous variable-level positive airway pressure (VPAP) is delivered through the interface device into the patient's airway during sleep to prevent airway obstruction. OSA is unique to all positive airway pressure (PAP) applications in that the patient is otherwise healthy and the therapy has to be a minimally obtrusive in order to not disrupt the patient while sleeping, whereas in other PAP applications disrupting sleep is of negligible concern. There are three different forms of NIV interface devices; Nasal Interfaces, Oral Interfaces and combined Oral-Nasal Interfaces. Of the Nasal Interface type, there are two categories: Nasal Masks and Nasal Interfaces or Cannulae.

Nasal ventilation interface devices are typically used for supplying supplemental oxygen gas to a person's lung during their natural breathing by placing the tips of the device within the person's nostrils or nares. These devices are constructed of tubing diameters substantially smaller than the diameter of the nostrils since the volumetric demand for the supplemental oxygen is very low (<2 LPM) negating the need for large bore tubes, and since the user must be able to breathe room air around the outside of the interface tubes prongs which are placed in the nostrils.

Oxygen nasal cannulae typically comprise a main base tube positioned horizontally under the nose from which two prongs extend at right angles upward and into the nostrils. With some devices, these prongs are designed to pinch the nostril septum to facilitate retention and sometimes are tilted toward each other at their tips to facilitate pinching.

Typically, if not always, the base tube has a through lumen and the oxygen supply tubing usually attaches to and extends from both sides of this base tube, typically routed around the ears then to the front of the neck to secure the apparatus to the patient. In addition to these oxygen interface tubes, a medical practice has been established to use larger nasal interface tubes that seal the nostrils in order to provide positive airway pressure (PAP) ventilation therapy. The practice is especially common in neonates because of the trauma associated with invasive tracheal intubation.

There are two basic forms of nasal interface tubes; non-sealing nasal interface tubes for supplemental oxygen therapy and sealing nasal interface tubes for PAP ventilation.

Recently special versions of sealing nasal interface tubes have been developed which are intended to improve PAP ventilation; however as shall be explained, these designs have significant deficiencies especially when used in OSA applications.

Agdanowski, U.S. Pat. No. 4,648,398 describes an expandable foam-tipped nasal prong wherein the user compresses the foam for insertion into the nostril then the foam re-expands to contact the nostril wall. The nasal prongs are right angle extensions from a base tube like oxygen therapy interface tubes. The Agdanowski device has two significant deficiencies especially when used in an OSA application: (1) The traditional base tube—right angle prong configuration is inherently resistant to flow because air which is forced into the base tube from both sides collides in the middle of the base tube and the air must make an abrupt directional change into the prongs. Generally, a resistant, turbulent design in an OSA application is undesirable because it causes extra noise (which is irritable to the user and bed partner) and because the user must compensate by increasing the pressure setting (which is less comfortable to the user). Increasing the pressure setting is more demanding on the seals, requiring the device to fit tighter to the user's nose (also less comfortable to the user). In non-OSA applications a resistive, turbulent design is acceptable since noise or higher pressure is of no concern to the user. (2) The Agdanowski device also does not allow the nasal prong portion to align correctly with the user's nostril canal.

However, alignment is key in OSA applications because unaligned prongs are uncomfortable. For example, Winthrop, U.S. Pat. No. 5,682,881 describes an interface tubes with an adhesive-backed foam strip placed on the skin below the nose for securing the interface tubes system in place. While adhesive backed securement systems are common is various short-term therapy applications, their viability in long term or repeated use is questionable. The Winthrop device also has the airflow resistance and alignment problems previously noted.

Trimble, U.S. Pat. No. 4,782,832 describes a nasal interface with a hard manifold positioned under the nose from which two frustoconical corrugated members extend for insertion into and sealing against the nostrils. The manifold is suspended below the nose by a bracket extending down from the forehead between the eyes and down the bridge of the nose. A gas supply tube is attached to the bracket. This bracket and manifold arrangement is an improvement for users who want the tubing away from their mouth or ears, however this configuration is obtrusive and not conducive to vision especially if wearing glasses. Additionally, discomfort from the hard plastic brackets and manifolds are common. Similar designs are described in Bordewick, et al., U.S. Pat. No. 6,418,928, and Bordewick U.S. Pat. No. 6,431,172. This family of devices is known commercially as the ADAM (airway delivery and management) Circuit or Nasal Pillows.

Wood, U.S. Pat. No. 6,478,026 describes a PAP nasal interface tubes comprised of a conventional oxygen interface tubes tubing configuration (a horizontal base tube positioned under the nose from which two prongs extend upward at right angles for insertion into the nostrils). The prongs comprise oval cross sections and a concentric ring at their tips. Similar designs are described in Wood, U.S. Pat. No. 6,595,215, Wood, U.S. Patent Application No. 2002/0092527, Strickland U.S. Patent Application No. 2003/0079749, and Wood, U.S. Patent Application No. 2003/0116163.

Interface tubes prongs with oval cross sections have been in commercial use since at least 1987, for example in Trimble, U.S. Pat. No. 4,782,832, however, an oval cross section has no practical value for PAP usage. The prong material must be significantly more compliant than the nostril tissue for the requisite comfort, and hence the nostril structure will shape the prong to conform to the nostril regardless of the shape of the prong. Indeed, in pediatric and adult applications, a prong with a circular cross section is as comfortable and seals as well as does an oval cross section prong, assuming they are both fabricated using the correct material softness.

Additionally, some of the devices have the problems of requiring deep interface cannulation of the prongs into the nose for sealing and retention; deep interface cannulation is highly undesirable to many users and may cause mucosal irritation or erosion. Finally, this family of inventions still possesses the nostril-prong alignment problems, flow turbulence problems, obtrusiveness, ear and cheek discomfort, and discomfort while user is lying on their side.

MacRae, U.S. Patent Application No. 2002/0046751 describes a medicine inhaler that has a waist-shaped tip that seals with the nostril. De Voss, U.S. Patent Application No. 2002/00446755 describes an oxygen nasal interface tubes with left and right nostril prongs that pinch the nasal septum in order to retain the device in place. Pinching is accomplished by tilting the distal tips toward each other and the tilt and spacing can be adjusted in order to produce enough pinching force to achieve retention. This design is unacceptable in many PAP applications, because a pinch force of greater than about 2 lbs. compression is required for adequate pinching in adults, which cannot be tolerated for extended durations. A slight amount of repeated or long term pinching can be tolerated (<1 lbs.), however this is insufficient for retaining an interface tubes in place.

Light nostril septum pinching by PAP nasal interface tubes has been previously successfully employed in the art described in Trimble U.S. Pat. No. 4,782,832 and Wood U.S. Pat. No. 6,478,026, however in these cases other primary retention features are used to secure the apparatus in place and septum pinching is a secondary retention feature and likely less than 1 lbs. compression.

Curti, U.S. Patent Application Serial No. 2002/0053346 describes a non-sealing oxygen nasal interface tubes with exhalation $CO_2$ sampling. The base tube between the nasal prongs is divided to create two separate tubing paths, one for oxygen delivery (inhalation) and one for $CO_2$ sampling (exhalation). This device has utility in anesthesia situations where $CO_2$ monitoring is necessary and its teachings and embodiments are considerably different than that which is required for PAP applications.

In summary there are five significant requirements of a PAP nasal interface tubes interface that are not adequately addressed in patient interface devices especially for OSA applications: (1) low resistance flow dynamics; (2) a comfortable and effective nostril seal without requiring deep penetration into the nose; (3) a simultaneously comfortable, unobtrusive and non-irritating system to retain the device to the nose, face and head; (4) a system or device that is easy to attach and remove; and (5) the overall apparatus must be minimally obtrusive, comfortable and ergonomic, allowing a user to speak, see, wear glasses, drink, and talk on the phone while being worn before falling asleep, and allowing the user to comfortably lay on their side during sleep without shifting the device or dislodging the portion that seals to the nose. Most of the prior art is useful and applicable only for PAP applications in which the patient is unconscious or heavily sedated thus unaware of the noted deficiencies.

As will be described in the subsequent sections, the present invention(s) disclosed herein solves the various deficiencies that exist with the currently available PAP nasal interface tubes devices, especially with respect to the requirements of an OSA user.

SUMMARY OF THE INVENTION

Disclosed in this invention is a unique PAP nasal interface tubes ventilation interface comprising: (1) nasal prongs that are arcuately curved and non-angulated to minimize flow resistance, turbulence and noise; (2) freely moveable prong alignment and spacing to permit optimal alignment of the prongs with the nostril foramen to optimize comfort to the user; (3) a nostril sealing cushion engageable with the nostril rim to effect sealing without deep interface cannulation; (4) a strap securement system that that provides (a) an upward compression force for the sealing cushions to stay engaged on the nostrils, and (b) that provides minimally obtrusive and maximally comfortable retention of the apparatus to the nose, face and head. Additional novel and unique features are also disclosed such as improved exhaust vent ports, mouth closure, concurrent supplemental oxygen delivery and aromatherapy.

In one aspect of the invention, a nasal ventilation interface including a pair of tubes configured to deliver a ventilation gas, the tubes attachable at a first end to a ventilation gas supply hose and engageable at a second end with a person's nostril; and a coupler configured to align the pair of tubes with the person's nostrils, wherein each tube has an absence of pneumatic interconnection with the other tube.

In another aspect of the invention, a kit comprising a pair of tubes configured to deliver a ventilation gas, the pair of tubes attachable at a first end to a ventilation gas supply hose and engageable at a second end with a person's nostril; a coupler configured to align the pair of tubes with the person's nostrils, wherein each tube has an absence of pneumatic interconnection with the other tube; and at least one pair of sealing cushions configured to be attachable to the second end of each ventilation interface tube and configured to impinge the nostril.

In a further aspect of the invention, an apparatus for supplying ventilation gas, the apparatus includes a connector configured to be attachable to a ventilation gas supply; a pair of tubes extending from the connector and configured to impinge a rim of a user's nostril such that a pressurized gas from the ventilation gas supply can be supplied to the person's respiratory system; and a coupler configured to align the pair of tubes with the person's nostrils, wherein each tube has an absence of pneumatic interconnection with the other tube.

In another aspect of the invention, a method of receiving a pressurized gas comprising positioning a ventilation interface device on a patient, the ventilation interface device comprising a pair of tubes configured to deliver a ventilation gas, the pair of tubes attachable at a first end to a ventilation gas supply hose and engageable at a second end with a person's nostril; a coupler configured to align the pair of tubes with the person's nostrils, wherein each tube has an absence of pneumatic interconnection with the other tube; and securing the ventilation interface with a first strap extending laterally over the ears from underneath the nose such that the first strap provides upward lift.

In one aspect of the invention, a nasal ventilation interface comprising a distal end configured to engage a user's nostrils; a proximal end configured to attach to a ventilation gas supply; and a mid-section between the proximal and distal ends, wherein the distal end and the mid-section comprises a pair of tubes having an arcuate non-angulated shape and having an absence of pneumatic interconnections between each of the tubes of the pair.

In a further aspect of the invention, a nasal ventilation interface comprising a pair of tubes configured to engage a user's nostrils at a distal end, wherein the distal end of the tubes comprise a substantially straight centerline axis, and further comprising a proximal end configured to attach to a ventilation gas supply hose; and a coupler configured to connect the pair of tubes having a movable joint between the pair of tubes, wherein the movable joint comprises a swivel to permit rotational movement of the tubes in at least one plane, wherein the movement is used to substantially align the axial centerline of each tube with a nostril foramen.

In another aspect of the invention, a nasal ventilation interface for the purpose of supplying ventilation gas to a person's airway, the interface comprising a generally tubular construction with a distal end configured with a first and a second tube for engagement with a person's nostrils, a proximal end configured for attachment to a ventilation gas supply hose, and a coupler connecting the first and second distal ends of the tubes, and further comprising a lifting means applied substantially directly under the nose to the distal end of the first and second tubes, wherein the lift creates and maintains an engagement force between the tubes' distal tip and the nostrils, and further wherein the lifting means comprises a first strap attached to the head over and behind the ears.

In a further aspect of the invention, a nasal ventilation interface apparatus for the purpose of supplying ventilation gas to a person's airway, the apparatus comprising a generally tubular construction with a distal end comprising a first and second tube configured to engage a person's nostrils, a proximal end configured to attach to a ventilation gas supply hose, wherein the distal end comprises a facial pad positioned between the tubes and the skin between the user's nose and upper lip, wherein the facial pad cushions the user's skin and tilts the distal end tubes in an angle in the sagittal plane wherein the angle aligns the distal end tubes with the rim of the user's nostril.

In another aspect of the invention, a nasal ventilation interface apparatus for the purpose of supplying ventilation gas to a person's airway comprising a generally tubular construction with a distal end comprising a first and a second tube configured to engage a person's nostrils, a proximal end configured to attach to a ventilation gas supply hose, further comprising a band member substantially circumventing the head from the chin to the top of the head, wherein the band applies upward compression on the chin so as to bias the mouth in a close state, and wherein the band comprises means to attach the apparatus to the band member.

The above aspects of this invention are more fully explained in reference to the drawings and general disclosure herein.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 7 shows a perspective view of various couplers as shown in

FIG. 6.

FIG. 14A shows a front view of a sealing cushion configured to seal against a rim of the nostril, including a stepped cushion profile for engagement and sealing to the nostril rim.

FIG. 14B shows a perspective view of the sealing cushion of FIG. 14A.

FIG. 14C shows a cross-sectional view of the sealing cushion of FIG. 14A along the line D-D.

FIG. 14D shows a perspective view of a sealing cushion.

FIG. 14E shows a cross-sectional view of the sealing cushion.

FIGS. 15A-15G show cross-sectional views of various sealing cushions according to a further embodiment of the present invention.

FIGS. 16A-16E show a cross-sectional view of the various sealing cushions along line E-E of FIG. 14D.

DESCRIPTION OF THE INVENTION

Nasal Interface

Figure 1:
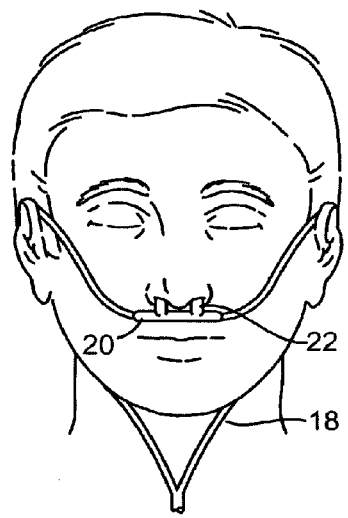
FIG. 1 shows a front view of a conventional nasal interface cannula for positive pressure ventilation.
Figure 2:
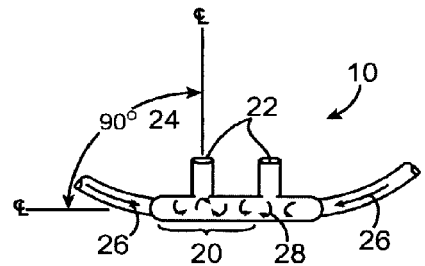
FIG. 2 shows a perspective view of the conventional nasal interface cannula of FIG. 1.

FIGS. 1 and 2 show a perspective view of a conventional positive airway pressure (PAP) nasal interface 10. The nasal interface 10 comprises a base manifold 20 positioned below the nose from which two nasal prongs 22 extend at right angles 24 upward into the nose. The base manifold 20 typically receives airflow 26 from both directions causing turbulent mixing and high resistance 28. The sudden directional change of the airflow up into the two nasal prongs 22 adds to the high resistance and turbulent flow 28 within the manifold 20.

Figure 3A:
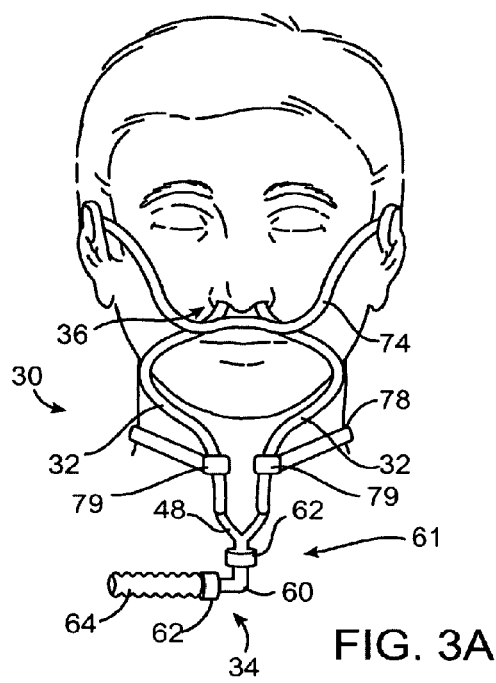
FIG. 3A shows a front view of a nasal interface according to one embodiment of the present invention.

FIG. 3A shows a perspective view of a nasal interface device 30 according to one embodiment of the present invention. The device 30 comprises a pair of ventilation interface tubes 32 which are configured to deliver a ventilation gas to a user. The tubes 32 are attachable at a first end 34 to a ventilation gas supply hose 64 and engageable with a person's nostrils at a second end 36. Each tube 32 has an absence of pneumatic interconnection with the other tube 32 providing laminar flow to the nostrils.

As shown in FIG. 3A, the ventilation gas supply hose 64 is attachable to the pair of tubes 32 with a bifurcation device 61. The bifurcation device 61 is preferably a Y-connector 48. However, it can be appreciated that other shapes and configurations can be used to bifurcate the gas supply hose into at least two tubes 32. The bifurcation device 61 also preferably comprises at least one swivel 62. As shown in FIG. 3A, the bifurcation device 61 can further include at least two swivels 62, a hose coupler 60 and the Y-connector 48.

The pair of tubes 32 preferably impinge the rim of the nostrils at the second end 36. As shown in FIG. 3A, the device 30 can be secured to the user by a combination of a first strap 74 in the form of a headband and a second strap 78 in the form of a neckband. The first strap 74 preferably attaches to the pair of tubes 32 just below the user's nostril by a suitable means. The first strap 74 preferably extends from just below the user's nostril and over the user's ears connecting behind the back of the user's head. It can be appreciated that the interface device 30 can be secured to the user's face by any suitable means.

In an alternative embodiment, a second strap 78 can be used to attach the interface device 30 to the neck area of the user. As shown, the second strap 78 is attachable to each of the tubes 32 at a location between the bifurcation device 61 and the second end of the device 36. The second strap 78 can preferably be attachable to the interface tubes 32 by any suitable means including a snap lock, Velcro, fabric loop, clip, and other suitable attachment devices.

Figure 3B:
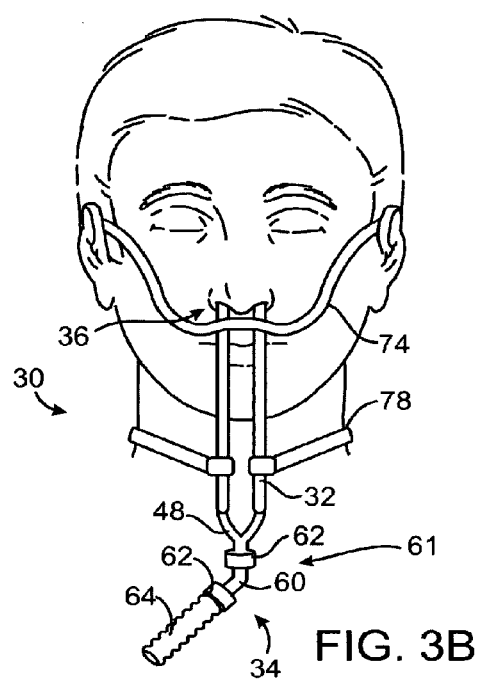
FIG. 3B shows a front view of the nasal interface of FIG. 3A according to another embodiment.

FIG. 3B shows a perspective view of another embodiment of the nasal interface device as shown in FIG. 3A. As shown in FIG. 3B, the ventilation gas supply hose 64 is attachable to the pair of tubes 32. The pair of tubes 32 extend directly from the bifurcation device 61 to the nostrils without an arcuate shape as shown in FIG. 3A.

The hose coupler 60 is configured to direct the gas supply hose 64 away from the body. The hose coupler 60 is preferably an angled member having an angle of approximately 90 degrees to approximately 180 degrees. As shown in FIG. 3A, the hose coupler 60 is a 90 degree angle. Meanwhile, the hose coupler 60 as shown in FIG. 3B has an angle of approximately 120 degrees.

Figure 4:
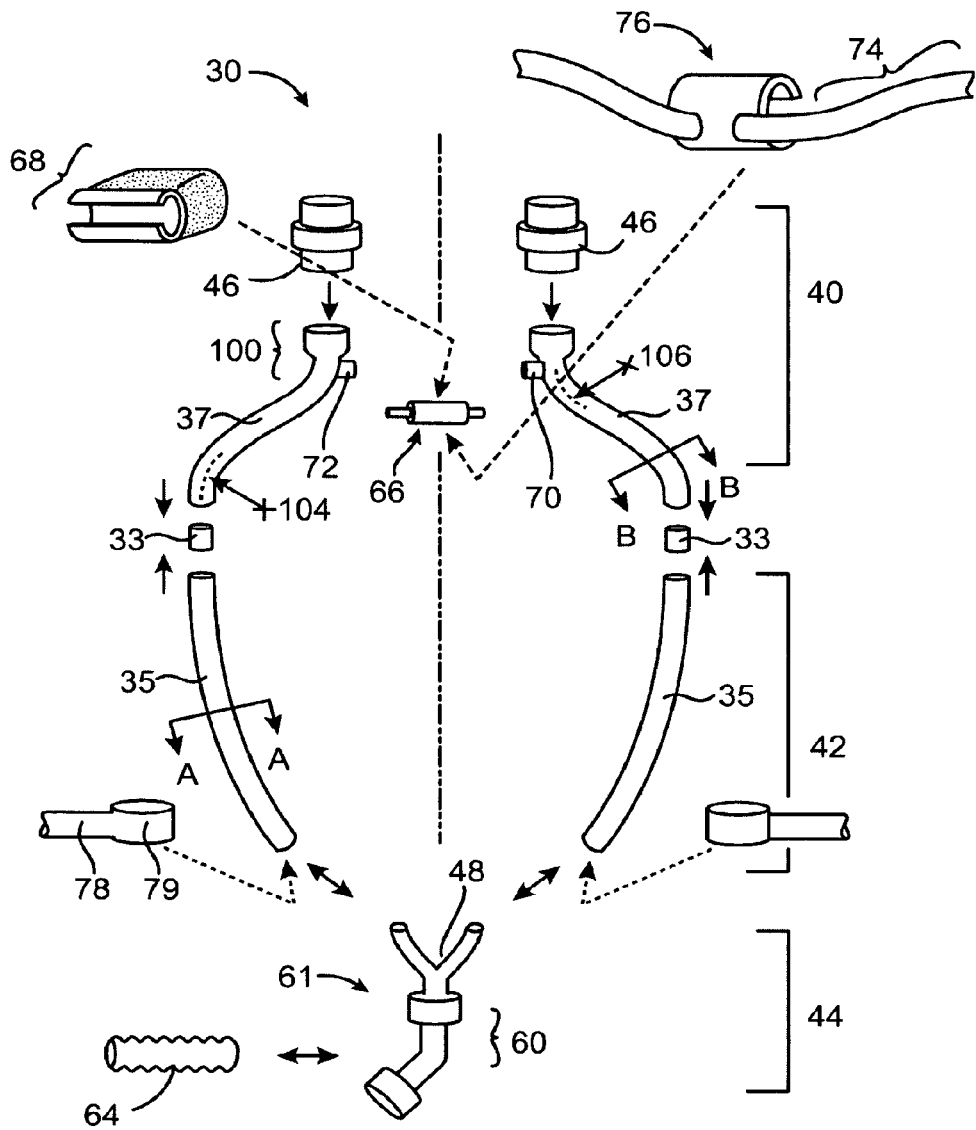
FIG. 4 shows an exploded perspective view of the nasal interface of FIG. 3A.

FIG. 4 shows an exploded perspective view of a nasal interface device 30 according to another embodiment of the present invention. As shown in FIG. 4, the device 30 is generally comprised of a tubular construction, and can be comprised of three basic sections; a distal section 40, a midsection 42 and a proximal section 44.

The distal section 40 comprises a pair of sealing members 46, a pair of delivery tubes 37, and a connector 33. As shown in FIG. 4, the pair of tubes 32 as shown in FIG. 3 can be separated into a pair of supply tubes 35 positioned within the midsection 42 of the device 10 and a pair of delivery tubes 37 positioned within the distal section 40 of the device 30. Alternatively, the pair of tubes 32 can be, as shown in FIGS. 3A and 3B, one continuous tube extending from the gas supply hose 64 to the distal end 36.

The pair of delivery tubes 37 can be configured to engage the rim of the user's nostril or nares or alternatively a pair of sealing members 46 can be attached to the distal end 36 of the delivery tubes 37. As shown, the supply tube 35 is preferably attachable to the ventilation gas supply hose 64 via a Y-connector 48 at one end and to the pair of delivery tubes 37 at the other end with the connector 33.

In a preferred embodiment of the present invention, the pair of interface tubes 32 comprising the pair of delivery tubes 37 and the pair of supply tubes 35 are unconnected pneumatically to each other. However, the pair of tubes 32 can be mechanically connected via a mechanical coupler 66. In addition, the interface tubes 32 are preferably void of abrupt angles from the proximal end to their distal end of each of the tubes 32. As shown in FIG. 4, the distal end of each of the interface tubes 32 preferably comprise a terminal section 100, which is axially substantially straight (but not necessarily absolutely straight) for engagement with or for minor insertion into the nostrils.

At the inferior base of these distal straight terminal sections 100 the interface tubes 32 assume the most gradual curvatures 104 and 106 as possible while still fitting within the anatomy. The interface tubes 32 may curve and extend away from the nostrils in several possible configurations. In the preferred configuration the interface tubes 32 curve first laterally 106 then inferiorly 104 toward the ventral aspect of the neck, typically lateral to the corners of the mouth. It can be appreciated that the tubes 32 are curve posteriorly. This curved non-angulated configuration minimizes flow resistance thus minimizing turbulence, leakage, noise and the required pressure level. Airflow resistance of this invention is approximately 25% less than that of conventional PAP nasal cannulae (which is more resistive for the reasons described previously).

In a further embodiment of the present invention as shown in FIG. 4, the distal section 40 of the device 30 is preferably equipped with a pair of sealing cushions 46 that impinge the nostrils. The sealing cushions 46 are attachable to a distal end of each of the pair of tubes 32. The sealing cushions 46 position the interface tubes 32 against the nostril rim to provide a leak free connection between the sealing cushion 46 and the interface tubes 32, and to prevent dislodgment of the sealing cushions during use. As shown in FIGS. 14, 15 and 16, the sealing cushions 46 can be configured in any suitable shape and cross-sectional design to insure proper sealing and comfort. The shape of the sealing cushions 46 including the cross-sectional design also provides comfort to the user.

The distal section 40 is preferably secured to the user by the first strap 74 or headband. As shown in FIGS. 3A and 3B, the first strap 74 preferably attaches to the pair of tubes 32 just below the user's nostril by a suitable means. As shown in FIG. 4, the first strap 74 is attachable to the interface tubes 32 via a connector 76. The first strap 74 preferably extends from just below the user's nostril and over the user's ears connecting behind the back of the user's head. It can be appreciated that the interface device 30 can be secured to the user's face by any suitable strap, band or retention device.

The connector 76 is preferably attached to the coupler 66 to secure the device 30 to the nose, face and head. An additional strap or second strap 78 can be provided for attachment of the interface tubing 32 in the mid-section 42 to the neck to help secure the device to the body. It can be appreciated that in an alternative embodiment, the mid-section 42 disconnects from at least the distal section 40, allowing separation of the interface tubing 32, as needed.

As shown in FIG. 4, the distal section 40 comprises a pair of sealing cushions 46, a mechanical coupler 66 and the second or distal ends of the pair of tubes 32. In a preferred embodiment of the present invention, the pair of interface tubes 32 is joined under the nose with the mechanical coupler 66. The coupler 66 is configured to adjust the spacing 120 (FIG. 6) of the pair of distal tips to match the user's anatomy.

It can be appreciated that in a preferred embodiment, immediately proximal to the soft sealing cushions 46, the pair of tubes 32 is attached with a coupler 66. A skin cushion or facial pad 68 can be attached to the coupler 66 or to one of the neighboring interface tubes 32 for the purpose of padding the skin to absorb strapping forces and aligning the angle of the distal tips of the device with the user's nostrils.

The mid-section 42 comprises symmetrical tubes of either the interface tubes 32 or as shown in FIG. 4 the supply tubes 37. If a second strap 78 is provided the supply tubes 37 are attached to the second strap 78 via a loop connector 79. It can be appreciated that the second strap 78 can be attached by any suitable connector to the interface tubes 32.

As shown in FIG. 4, at the proximal end 44, the pair of tubes 32 joins at a bifurcation site 48. The bifurcation site 48 is preferably substantially proximal to the distal end 36. However, it can be appreciated that the bifurcation site 48 does not have to be substantially proximal to the distal end 36 and can be positioned more distal to the distal end 36 of the device 30. Between the distal tip and the bifurcation site 48, the device 30 is comprised of generally symmetric construction. Preferably, the pair of tubes 32 is not in communication pneumatically other than at the site of bifurcation 48.

The nasal interface device 30 is preferably made of biocompatible, hypoallergenic materials or other suitable materials. In addition, the device 30 can be treated with antimicrobial, hydrophilic or lubricious surface treatments to prevent unfavorable tissue response.

The interface tubes 32 including the supply tubes 35 and delivery tubes 37 are preferably made of material such as polyvinyl chloride (PVC), plastisol, silicone, urethane, urethane-PVC blends, synthetic thermosets or combinations thereof. It can be appreciated that the device 30 can be made from any suitable material.

The interface tubes 32 preferably have an inner diameter of about 8 mm to about 16 mm for adults, about 5 mm to about 8 mm for pediatrics, and about 1 to about 5 mm for neonates. In addition, the interface tubes 32 preferably have a durometer of about 30 A Shore to about 80 A Shore for the tubes 32 and a durometer of about 10 A to about 70 A for the distal end 36 and/or sealing cushions 46.

Figure 5A:
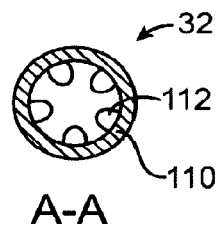
FIG. 5A shows a cross-sectional view of the nasal interface of FIG. 4 along the line A-A.
Figure 5B:
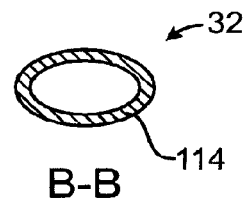
FIG. 5B shows a cross-sectional view of the nasal interface of FIG. 4 along the line B-B.

FIGS. 5A and 5B show a preferred embodiment of a cross-sectional view of the pair of interface tubes 32 in the distal section 40 and the mid-section 42 of the device 30, respectively. As shown in FIG. 5A, the cross-sectional shape of the tubing 32 at the mid-section 42 is round 110. However, it can be appreciated that the cross-sectional shape of the distal section 40 or mid-section 42 of the interface tube 32 can include longitudinal or radial ribs 112 to prevent kinking. As shown in FIG. 5B, the interface tubes 32 in the distal section 40 preferably have a flatter profile 114 so as to be less obtrusive to the user, or can comprise radial corrugations in strategic locations to provide flexure of the device 30 to mate with the individual's anatomy. Alternatively, the device 30 can comprise shape-memory or malleable shape-able members within its construction to allow the pair of interface tubes 32 to be curved optimally to fit the individual's anatomy.

Preferably, the distal section 40 of the nasal interface device 30 is injection molded to its final shape. However, the distal section 40 can be extruded or injection molded straight then bend-formed to its final shape, or dip formed, or can be shapeable by the user. The proximal section of the device 30 is preferably extruded and optionally bend-formed into the desired curved shape that matches a stereotypical chin and neck anatomy. It can be appreciated that the combination of injection molding, extruding or injection molded straight and then bend-formed into the desired shape can be used to manufacture the interface device 30.

Figure 6:
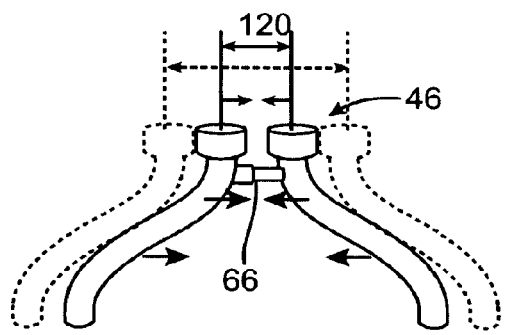
FIG. 6 shows a perspective view of a coupler according to one embodiment of the present invention.

FIG. 6 shows a perspective view of a portion of the distal section 40 of the device 30. As shown in FIG. 6, the distal section 40 comprises a pair of sealing cushions 46 and the second or distal ends of the pair of interface tubes 32. In a preferred embodiment of the present invention, the pair of interface tubes 32 is joined under the nose with a mechanical coupler 66. The coupler 66 is configured to adjust the spacing 120 of the pair of distal tips or sealing cushions 46 to match the user's anatomy.

The coupler 66 is preferably a plastic tubular member of approximately 60-80 Shore A durometer. The coupler 66 is preferably extruded and then formed to create the joints, or alternatively injection molded.

Figure 7:
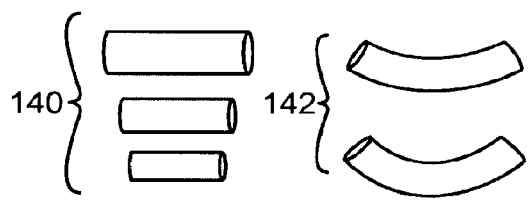

As shown in FIG. 7, the coupler 66 can be removably attached to the interface tubes 32 in which case there may be a variety of sizes 140 or shapes 142. The variety of sizes 140 or shapes 142 can be select based on the user's anatomy.

Figure 8A:
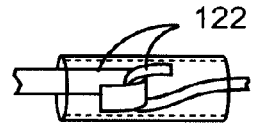
FIGS. 8A-8G show perspective views of the coupler according to FIG. 6 having various method of adjusting the length of the coupler according to various aspects of the present invention.
Figure 8B:
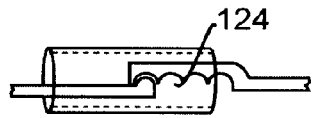
Figure 8C:
Figure 8D:
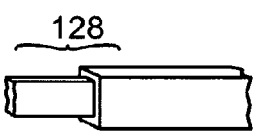
Figure 8E:
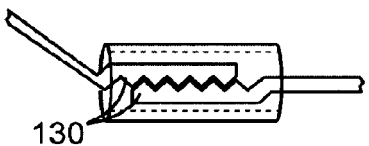
Figure 8F:
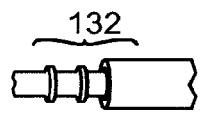
Figure 8G:
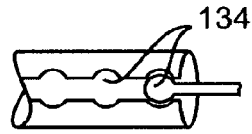

Alternatively, as shown in FIGS. 8A-8G, the coupler 66 can be permanently affixed to the pair of interface tubes 32, in which case the coupler 66 preferably comprises an adjustment feature to adjust or change the length of the coupler 66. The length of the coupler 66 can be adjusted by the use of opposing hooks 122 (FIG. 8A), a ratchet 124 (FIG. 8B), a threaded system 126 (FIG. 8C), a tongue and flat groove 128 (FIG. 8D), an opposing saw tooth 130 (FIG. 8E), opposing connectable tubes 132 (FIG. 8F), or a ball and socket 134 (FIG. 8G). It can be appreciated that the length of the coupler 66 can be adjusted using any suitable device.

Figure 9:
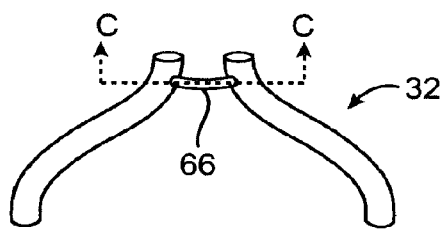
FIG. 9 shows a perspective view of an alternative embodiment of the coupler, wherein the coupler has a lumen that communicates pneumatically with the tubes of the interface device.
Figure 10:
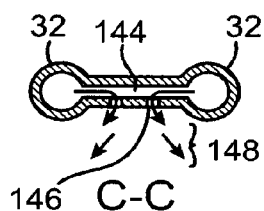
FIG. 10 shows a cross-sectional view of the coupler of FIG. 9 along the line C-C.

In an alternative embodiment as shown in FIGS. 9 and 10, the coupler 66 can further comprise a lumen 144 that communicates pneumatically with the pair of interface tubes 32. The lumen 144 is preferably substantially smaller and more resistive to airflow than the interface tubes' main lumen so as to limit airflow into the coupler to avoid generating backpressure into the interface tubes 32 lumens. However, it can be appreciated that the lumen 144 can be substantially smaller, smaller, equal or substantially larger than the interface tubes 32 main lumen. In addition, it can be appreciated that the coupler lumen 144 can include exhaust vent ports 146 allowing venting of an exhaled gas 148 and $CO_2$ out of the coupler 66.

Figure 11A:
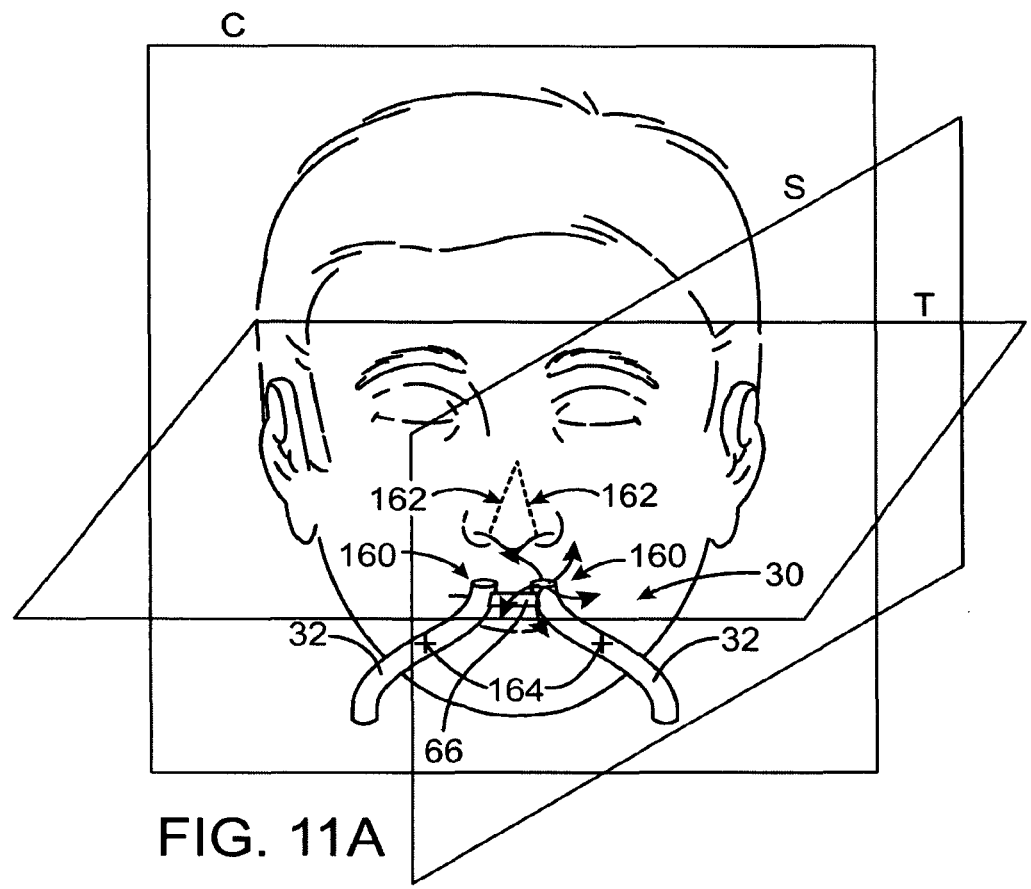
FIG. 11A shows a plan view of various angle of adjustment of the interface tubes configured to align the tubes with the nostrils of the nose.
Figure 11B:
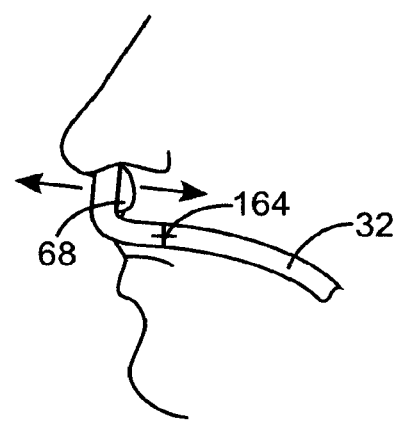
FIG. 11B shows a side view of the various angles of adjustment of the interface tubes of FIG. 11A.

FIGS. 11A and 11B show a front and side view of the interface device 30 based on a user's facial anatomy. As shown in FIGS. 11A and 11B, the second or distal ends 36 of the interface tubes 32 can swivel in multiple planes from a roughly fixed origin 164 in order to align the centerline axis of the distal tips 160 with the centerline axis of the nostril canals 162. Because there is a vast variety of nose shapes, sizes, and angles, and because proper alignment is essential for comfort, angle adjustability in multiple planes is essential especially in OSA applications. In order to achieve a proper alignment, the interface tubes 32 can swivel in the sagittal plane S, the coronal plane C and the transverse plane T.

As shown in FIGS. 11A and 11B, the sagittal plane S generally relates to the suture between the parietal bones of the skull or situated in or being in the medial plane of the body or any plane parallel thereto. The coronal plane C relates to lying in the direction of the coronal suture or relating to the frontal plane that passes through the long axis of the body. Meanwhile, the transverse plane T is at right angles to the anterior-posterior axis of the body.

Figure 12:
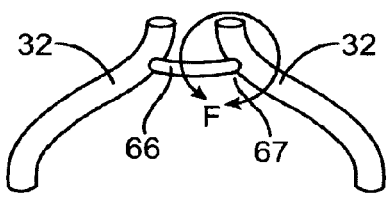
FIG. 12 shows a perspective view of the connection between the coupler and interface tubes.
Figure 13A:
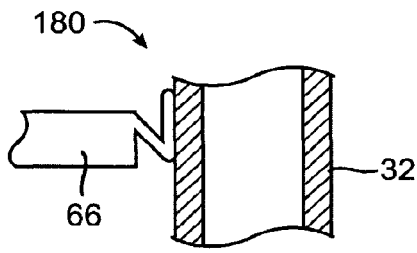
FIGS. 13A-13H show cross-sectional views of various connections between the coupler and interface tubes of FIG. 12.
Figure 13E:
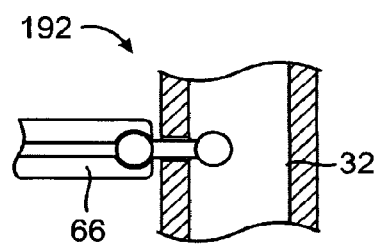
Figure 13B:
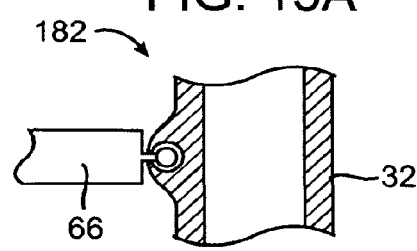
Figure 13F:
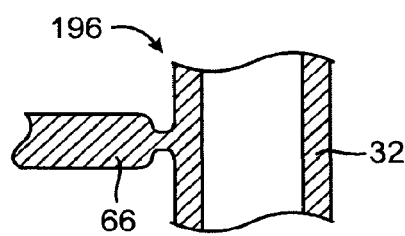
Figure 13C:
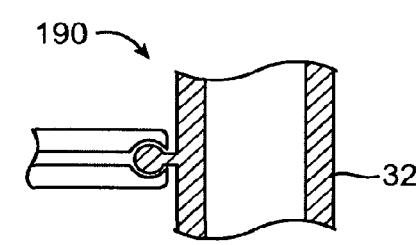
Figure 13G:
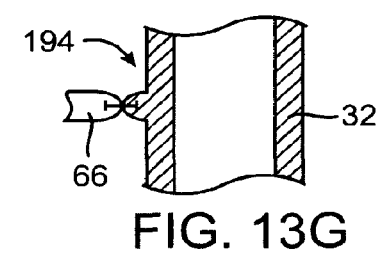
Figure 13D:
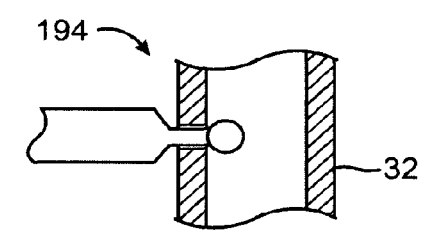
Figure 13H:
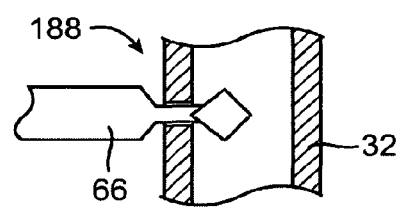

FIG. 12 shows a perspective view of another aspect of the present invention further comprising a movable joint 67 between the coupler 66 and the distal end of the interface tubes 32. The movable joint 67 allows free movement of the distal end of the interface tubes 32 in order to permit alignment of the sealing members 46 and the rim or entrance of the nostril canals.

As shown in FIGS. 13A-13H, the movable joint 67 can be a hinge joint 180 (FIG. 13A), a ball and socket swivel joint 182 with the ball attached to the interface tubes 32 (FIG. 13B), a ball and socket swivel joint 190 with the ball attached to the coupler 66 (FIG. 13C), a gliding joint 194 with a coupler ball inserted into the interface tubes lumen (FIG. 13D), a combination of a ball and socket swivel joint with a glide joint 192 (FIG. 13E), a pivot joint 196 optionally with an inserted tie bar (FIG. 13F), a gliding joint with a catch feature inserted into the interface tubes lumen 188 (FIG. 13H), a flex joint 194 (FIG. 13G), or any combinations thereof. It can be appreciated that the movable joint 67 can be any suitable joint and that the embodiments as provided are examples only.

The joints between the interface tubes 32 and the coupler 66 can be insert molded, bonded or press fit into the respective components.

FIG. 14A shows a front view of the distal tips 100 of the interface tubes 32, which are equipped with sealing cushions 46. As shown in FIG. 14A, the sealing cushions 46 and seal the nostril. In addition, the sealing cushions 46 prevent the interface tubes 32 from penetrating deep into the nostril. The sealing cushions 46 are preferably removably attachable from the interface tubes 100.

As shown in FIG. 14A, the sealing cushions 46 and the interface tubes 32 are designed to assure (1) proper positioning of the sealing cushion 46 against the nostril rim, (2) a leak free connection between the sealing cushion 46 and the interface tubes 32, and (3) prevent inadvertent dislodgement of the sealing cushion 46 during use.

FIG. 14B shows a perspective view of a sealing cushion 46 and distal end 100 of the interface tubes 32, comprising a step 202, a ridge 204, a groove 206, and a button or hook 208. The sealing cushion 46 can include a leash 210 (FIG. 14D) for grasping so that the sealing cushion 46 is easily installed and removed.

As shown in FIG. 14E, the sealing cushion 46 preferably extends 220 beyond the terminal section 100 of the interface tubes 32, such that the sealing cushion 46 enters the nostril rather than the terminal section 100 of the interface tube 32. It can be appreciated that the sealing cushions 46 can have any suitable cross sectional shape that provides a seal against the nostril of the noses. Thus, any variety of cross sectional shapes can be implemented and that the cross sectional shapes shown are only a few of the cross sectional shapes.

The sealing cushions 46 are preferably comprised of a soft thermoset or thermoplastic material of 45-60 Shore OO durometer. In addition, the sealing cushions 46 are preferably translucent or tinted to make it aesthetically pleasing or color coded, wherein each color is associated with a size and/or cross-sectional shape. The seal cushions 46 can be formed by extruding then shape forming, or by dip-molding or injection molding.

As shown in FIG. 14E, the terminal section 100 of the interface tubes 32 comprise an interface tube tip 222 position on the distal end of the interface tubes 32. The interface tube tip 222 is preferably of thinner wall thickness 224 than the thickness 226 of the balance of the interface tubes 32 to decrease the rigidity of the terminal section 100 in the event the tip is felt by the nostril.

FIG. 14C shows a stepped profile of a sealing cushion 46 with a first diameter 230 at the distal tip 235 and a second diameter 232 larger than the first diameter 230 at distance 234 from the distal tip 235. The larger diameter 232 is sized to be larger than a diameter of a nostril opening 236 and the smaller tip diameter 230 is designed to be approximately equal to or slightly less than the inner diameter of the nostril opening 236. Thus, the configuration seals on the outside rim 238 of the nostril and optionally seals along a depth on the inside surface 240 of the nostril. As shown, the engagement depth 234 is kept relatively shallow, preferably at a depth equal to about 5% to about 70% of the nostril diameter, and more preferably at a depth equal to about 20% to about 30% of the nostril diameter. However, it can be appreciated that the penetration can be greater or less than the diameters set forth above.

In addition, as shown in FIGS. 15A-15G, shape of the sealing cushion 46 is not limited to the configuration as shown in FIGS. 14A-14E. For example, the sealing cushions 46 can comprises a convex profile that curves inward 250 whereupon the nostril rim engages 252 on the curved inward surface (FIG. 15A), or a flared shaped sealing cushion 254 which at the distal tip flares to a larger diameter 256 than the base of the flare 258 such that the flared diameter seals on the inside diameter of the nostril at a distance in from the nostril rim (FIG. 15B), a double seal 260 (FIG. 15C), a mushroom profile 262 (FIG. 15D), a waist profile 264 (FIG. 15E), a reverse barb profile 272 (FIG. 15F), or a profile sealing around the outside of the nose 278 (15G).

Alternatively, the cross sectional profiles of the sealing cushions 46 can vary to match the anatomy depending on individuality variances. For example, the cross sectional profile of the sealing cushion can be circular 280 (FIG. 16A), an oval 282 (FIG. 16B), an arcuate 284 (FIG. 16C), an L-shaped 286 (FIG. 16D), an elliptical 288 cross sectional shape (FIG. 16E), or alternatively the cross sectional shape throughout the length of the cushion may vary. It can be appreciated that selection of different sizes and shapes can be available to optimize fit and comfort, as well as adjustability of the design, and the cushions may be shape-able by the user to match the desired shape.

Figure 17:
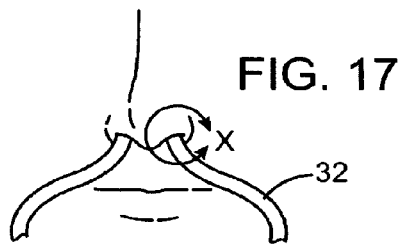
FIG. 17 shows a front view of another aspect of the sealing cushion.
Figure 18A:
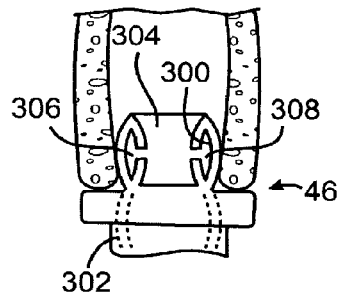
FIGS. 18A-C show a cross-sectional view of another aspect of the sealing cushion, wherein the sealing cushions are inflatable, application of a vacuum, and where the sealing cushion is part of the interface tubes, respectively.
Figure 18B:
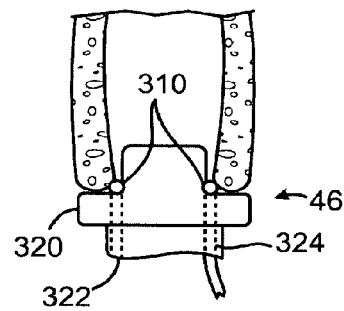
Figure 18C:
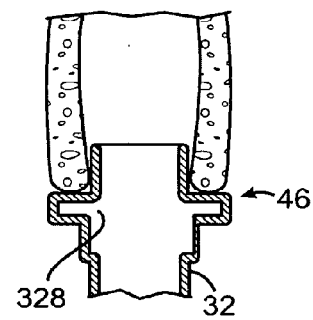

FIG. 17 shows a front view of another aspect of the sealing cushion 46, wherein the sealing cushions are inflatable (FIG. 18A), an application of a vacuum to the sealing cushion 46 is use (FIG. 18B), and where the sealing cushion 46 is part of the interface tubes 32 (FIG. 18C).

FIG. 18A shows a cross-sectional view of the sealing cushion 46, as shown in FIG. 17 in the area of nostril (X) that partially dilates or inflates 300 to seal against the nostril wall. Inflation can be performed by an inflation channel 302 communicating with the cushion, or by pressurization from the inside of the interface tube lumen 304 into the cushion space 306.

FIG. 18B shows a cross-sectional view of an alternative embodiment wherein the seal between the interface tube tip (or cushion) 320 and nostril wall is enhanced by application of a vacuum to the space between the interface tube and the nostril wall, either on the inside of the nostril or at the outside rim of the nostril 310 where continuous suction will not irritate the skin. Vacuum is delivered to the site through channels 322 in the interface tubing or through a separate vacuum tube 324. When applied, the vacuum sucks the nostril wall tissue into contact with the sealing cushion to create the seal.

FIG. 18C shows a cross-sectional view of a further embodiment in which the sealing cushion 46 is permanently connected to the nasal interface tubing 32, which may be more economically viable in single-use disposable applications such as emergency use. This one-piece design can be constructed by two pieces bonded or welded together or by a unitary design where the interface tubing material is thinned and reshaped 328 at the very tip to create the necessary softness and sealing shape.

Figure 18D:
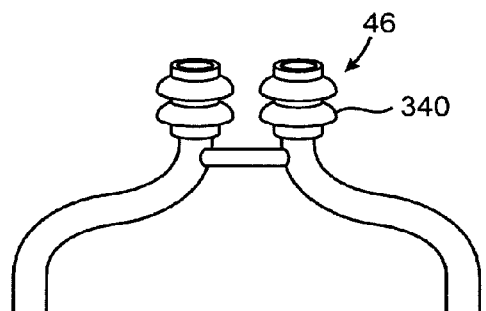
FIG. 18D shows a perspective view of a further aspect of the sealing cushions, wherein the sealing cushions are comprises of at least one ring.

FIG. 18D shows a perspective view of another embodiment of the sealing cushions 46, which are configured to fit within the nostril. As shown in FIG. 18D, the sealing cushion 46 comprises at least one disk 340, which is configured to fit within the nostril. The at least one disk 340 retains the sealing cushion 46 and tube 32 within the nostril by applying a minimum amount of pressure on the inside of the nostril. In order to spread out or distribute the force against the inside of the nostril, the sealing cushions 46 preferably comprises a plurality of disks 340. As shown in FIG. 18D, the sealing cushions 46 comprises two disks 340 having a downward shape or mushroom appearance.

Figure 18E:
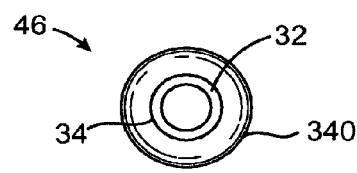
FIG. 18E shows a top view of a sealing cushion of FIG. 18D.

FIG. 18E shows a top view of the sealing cushion 46 of FIG. 18D. As shown, the sealing cushion 46 comprises at least one disk 340 extending around the lumen 34 of the sealing cushion 46.

Figure 19A:
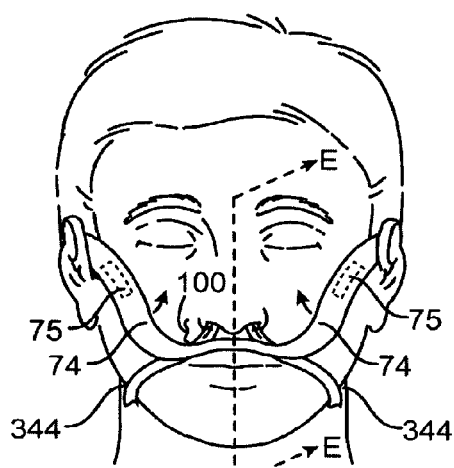
FIGS. 19A and 19B show a front and side view of a head strap configured to lift and compress the sealing cushions against the nose and secures the position of the interface tubes lateral to the nose.
Figure 19B:
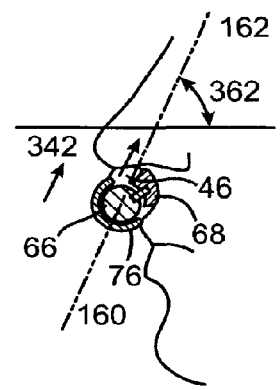

FIGS. 19A and 19B show a front view and a side view, respectively of a first strap 74, which connects to the coupler 66 at a rotational orientation at about 360 degrees opposite the nostril opening. The first strap 74 extends bilaterally, preferably over the ears, and is joined behind the head. The attachment orientation and overall configuration thus produces an upward lift 342 on the distal tips 235 of the sealing cushions 46 against the nostrils, thus compressing and retaining the sealing cushions 46 against the nostrils to facilitate and maintain a seal. The first strap 74 presses the interface tubes 32, lateral to the nose, against the skin 344 to help prevent inadvertent shifting of the interface tube 32 and the sealing distal tips.

The first strap 74 aides in retention of the device 30 to the user's face. Preferably at least a portion of the first strap 74 comprises an elastomeric material, such as a translucent highly elastic thermoset or thermoplastic material to enhance comfort and to reduce intrusiveness. Meanwhile, the balance of the first strap 74 is comprised of a fabric, such as a woven rubber-nylon blend. Alternatively, it can be appreciated in a further embodiment, the first strap 74 can further be comprised of a material, which provides padding on the skin side of the first strap 74, especially at the ear area or under the nose to further improve comfort. The attachment 76 to the coupler 66 can be a half-pipe that snaps onto a tubular-shaped coupler, or a snap, or a spring type catch, a loop or other easy attachment means, or the first strap 74 and coupler 66 can be permanently affixed together.

Figure 20A:
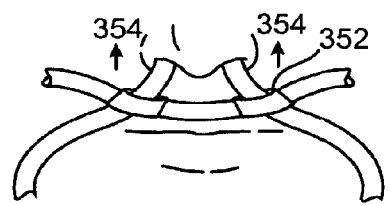
FIGS. 20A and 20B show front views of the head strap of FIGS. 19A and 19B.
Figure 20B:
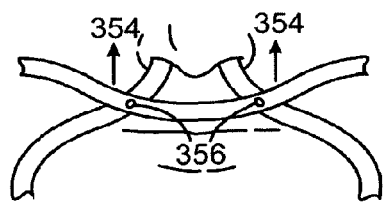

Alternatively, as shown in FIGS. 20A and 20B, the first strap 74 can include a slot 352 through which the distal ends of the interface tubes 32 pass (FIG. 20A), or a quick connect connection 356 to the interface tubes 32 (FIG. 20B), in order to provide additional lifting of the interface tubes lateral to the nose 354 to facilitate and maintain positive engagement with the nostril for sealing and overall apparatus retention. These attachment means may be floating attachments allowing some degree of motion between the interface tubes and the strap or may be non-floating. It can be appreciated that while certain specific aspects of the strap are disclosed, its uniqueness of lifting the distal tips against the nose for maintaining seal compression can be provided with a variety of attachment sites, fastening designs, and strap materials. In addition, the construction of the first strap 74 can include a shape memory or a shapeable member 75 to facilitate positioning and security of the device without sacrificing comfort.

FIG. 19B also shows a further embodiment of the present invention in which a nose or facial pad 68 is located under the nose to tilt the angle 362 of the distal end of the interface tubes 32, relative to the face, so as to align the angle 160 of the interface tubing distal tip 235 with the angle of the nostril canals 162 in the Sagittal plane. The pad 360 preferably comprises a soft, deformable material such as a jell or a shape memory energy absorptive material such as a viscoelastic foam.

The pad 68 can be attachable to the coupler 66 and or to the pair of interface tubes 32 directly under the nose and the attachment location is preferably keyed to assure proper orientation when connecting to create the upward lift 342 in the desired vector.

The nose or facial pad 68 is preferably formed of a malleable material with an adherent surface, which is placed over the nose and shaped into a shape that prevents over-distention of the nostrils from the pressure being extended upward on the nostrils by the nasal interface. Alternatively, ear loops or a head strap can retain the pad 68.

Alternatively, a variety of pad sizes can be available to the user to select the correct tilt setting, or the pad 68 itself can be adjustable. It can be appreciated that the pad 68 can be an integral part of the coupler 66, the head strap connector 76, interface tubes or sealing cushions 46, or the pad 68 and head strap connector 76 can connect to each other around or through the coupler 66. It can be appreciated that the pad can be attached to the head strap connector with a hinge such that the two snap together around the coupler.

Figure 21A:
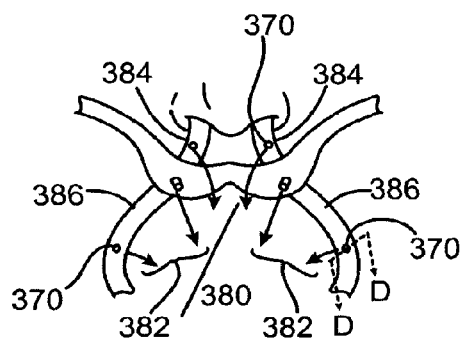
FIGS. 21A and 21B show a front and side view of exhaust vent ports angulated to be co-linear with the natural directional vector of exhaled gas.
Figure 21B:
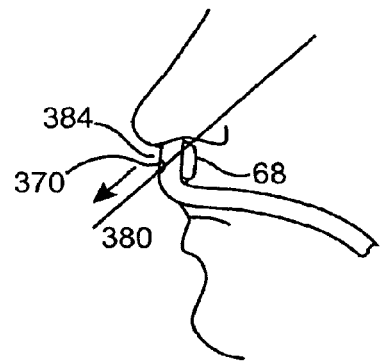

FIGS. 21A and 21B show a front and side view, respectively of another aspect of the present invention comprising ventilation exhaust vent ports 370. The exhaust vent ports 370 are generally used in a CPAP or VPAP patient interface applications since these systems do not include exhalation valves. The vent ports 370 lower the $CO_2$ levels inside the interface tubes 32 of the device 30, thus facilitate exhalation. In addition, the vent ports 370 provide a safety access to ambient air in the case of a gas source supply interruption.

As shown in FIGS. 21A and 21B, the vent ports 370 are configured in a diagonal orientation 380 with respect to the user's face so as to create a flow direction 382 outward from the face and downward from the nose, thus simulating the natural direction of nasal exhaled flow and directing the flow away from the user's face and not in the direction of the bed partner. The vent ports 370 can be located in the interface tubes 32 directly below the nose 384, or further proximally near the cheek 386.

Figure 22:
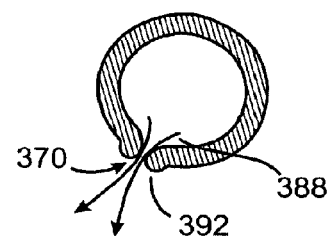
FIG. 22 shows a cross-sectional view of the exhaust vent ports of FIGS. 21A and 21B.

In a preferred embodiment, as shown in FIG. 22, the vent ports 370 are further configured for proper flow dynamics and entry effects (e.g., a chamfered or rounded leading edge 388) and there may be filtering for noise abatement (e.g., a low flow resistance filter integrated into the vent ports). The wall in the interface tubes 32 can be thickened 392 in the area to facilitate proper configuration and performance of the channels. It can be appreciated that the device 30 can be devoid of the vent ports 370 when used for PAP applications in which there is an exhalation valve in the tubing circuit.

Figure 23A:
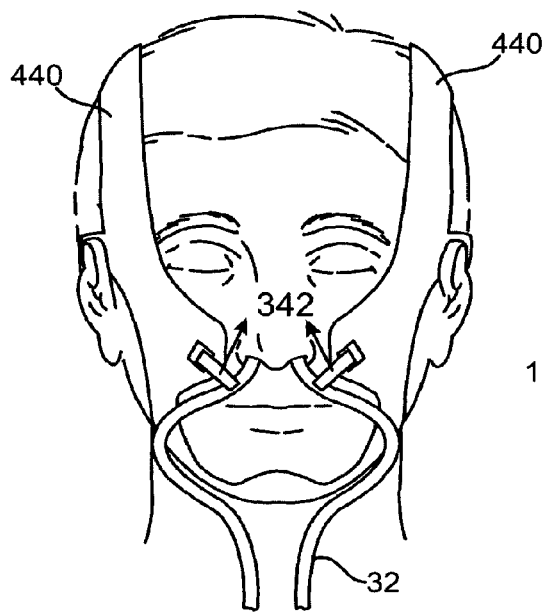
FIGS. 23A and 23B show a front and side view of a mandibular lift headband.
Figure 23B:
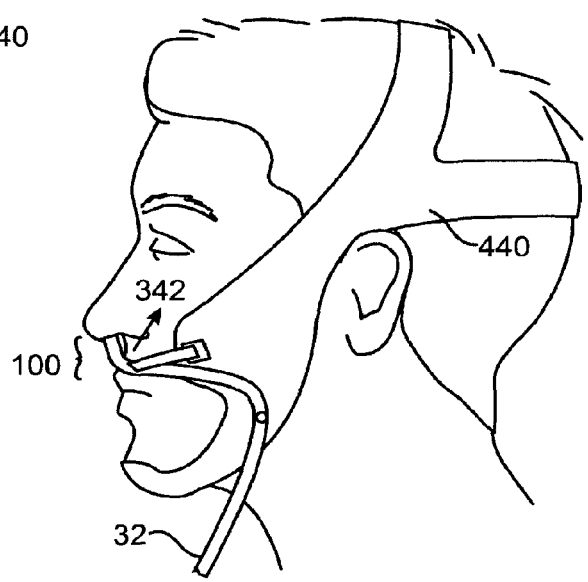

FIGS. 23A and 23B show a front and side view, respectively of a headband 440. The headband is configured to secure the interface tubes 32 in place while preventing the mandible 442 from opening in order to prevent mouth leaks. The headband 440 positions the distal end 100 of the interface tubes 32 to provide an upward lifting force 342 on the interface tube distal tips 100 such that the tips are compressed against the nostril to maintain a seal. The headband 440 can be an adjustable design to meet a variety of anatomies, or can be available in a variety of sizes. The headband is preferably comprised of an elastomeric of stretchable foam type material such as neoprene.

In another embodiment, a conduit or tube can be integrated into the interface tubes 32 of the device 30 for the purpose of supplying supplemental oxygen concurrent with the PAP therapy. Alternatively, the conduits or tube can be integrated into the interface tubes 32 of the device 30, which are connected to a vacuum source for the purpose of scavenging $CO_2$ rich air within the tubes 32 of the device 30. A mouth shield can be used, which is interconnected to the device and placed in the mouth for the purpose of blocking inadvertent leakage of the PAP air. It can be appreciated that a therapeutic or relaxing aromatic scent can be injected into the ventilation gas supply, preferably be inserting a cartridge into a receptacle in-line with the device's ventilation supply tubing.

It can be appreciated that the nasal interface device 30 as shown in FIGS. 1-23 can comprise any, some or all of the described embodiments. Also, while most of the embodiments described relate to long term or repeated use of the device, such as with OSA, it can be appreciated that there are non-OSA ventilation uses that would also benefit from these embodiments, such as PAP therapy for COPD, anesthesia recovery, mechanical ventilator weaning, outpatient surgery use, and emergency ventilation. Further, it should be appreciated that in addition to CPAP or VPAP ventilation, the invention can be used for other forms of mechanical ventilation such as CMV, SIMV, etc. Finally it should be appreciated that with the necessary modifications, the device can be reusable or disposable and can be adapted for adult, pediatric or neonatal use.

Figure 24:
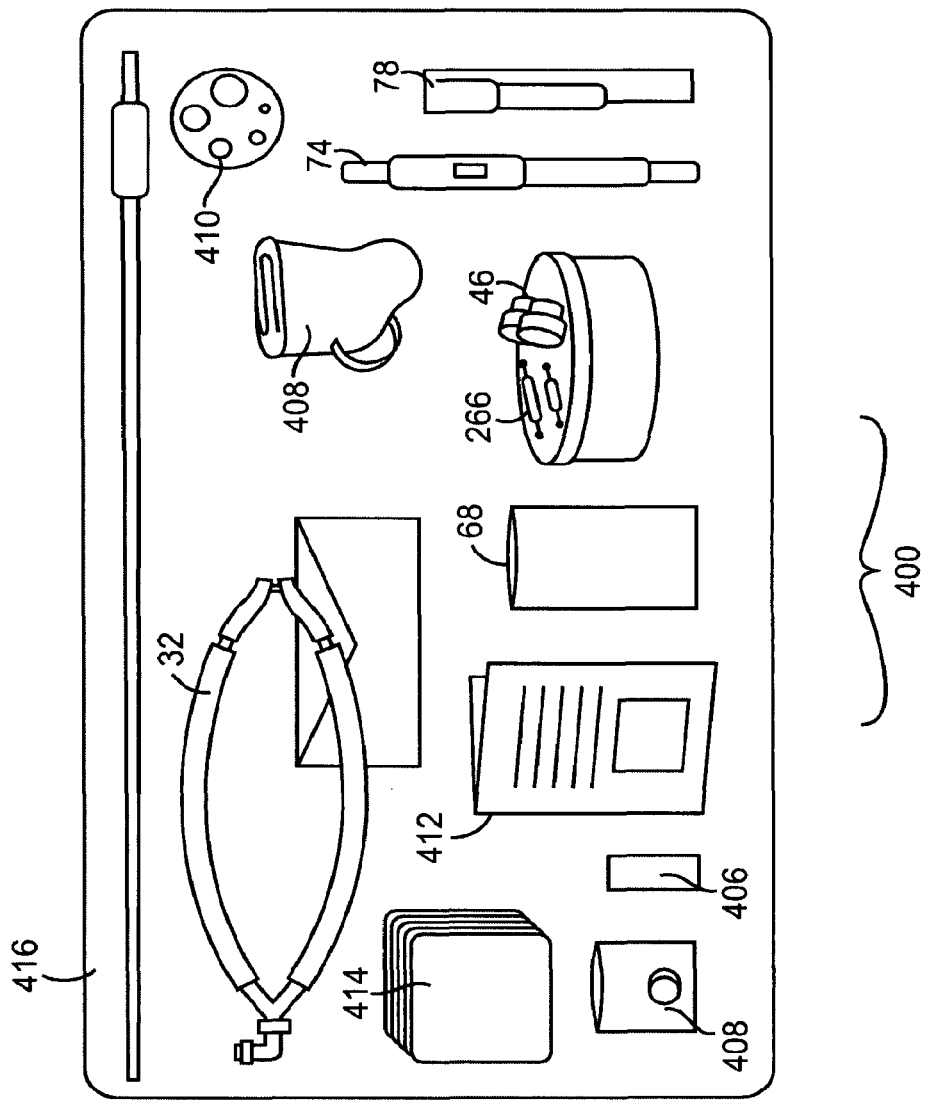
FIG. 24 shows a plan view of a nasal interface kit.

FIG. 24 shows a nasal interface kit 400 comprising a pair of nostril sealing cushions 46, a pair of interface tubes 32, a coupler 66, a first strap 74, a spare coupler 66, skin pads 68, a second strap 78, a cleaning and storage container 404, skin ointment 406, aroma therapy cartridges 408, a sizing gage 410, instruction sheet 412, an interface storage bag 414, a chin/mouth closure head band 418, and a package 416 for the individual components.

Nasal Mask Interface

Figure 25:
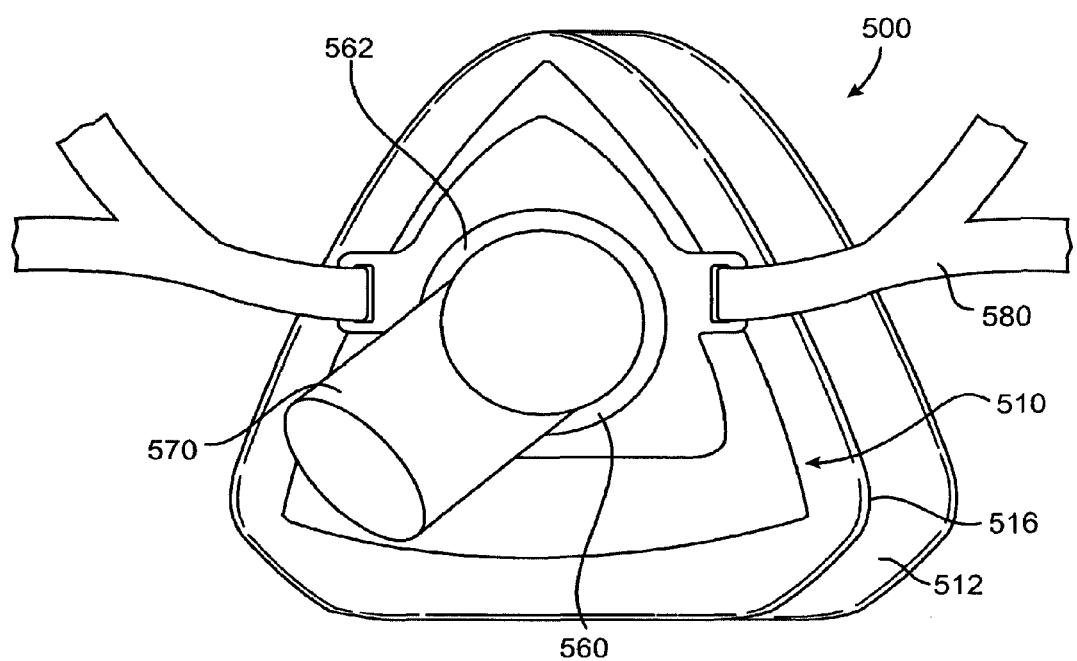
FIG. 25 shows a perspective view of a nasal mask for use with a ventilation system.

FIG. 25 shows a perspective view of a nasal mask 500 for use with a CPAP or VPAP ventilation system. The mask is preferably triangular shaped with a plastic concave shell 510 and a seal 512 extending around the perimeter on the concave side (for contacting the face). The seal 512 is preferably a shape-memory compressible foam member, which is attachable to a posterior base 514 (as shown in FIGS. 26A-26I) of the mask's plastic concave shell 510. The shape-memory compressible foam member can be either permanently or removably attached to the posterior base 514 of the shell.

The seal 512 is generally a strip of approximately ⅜" to approximately 1" wide, and approximately ½" to approximately 1⅔" in height extending around the perimeter 516 of the generally triangular shell 510. It can be appreciated that the face side of the seal 512 is generally a planar surface; however, it can comprise undulations and curvatures matching the general anatomy of the nares or surrounding structures.

Preferably, the foam member of the seal 512 is a viscoelastic foam with a shape memory that is compressibly deformable such that the foam material can be compressed against the face without the material extruding, bending or flexing in directions normal to or diagonal to the compression direction.

The compressibility (and volumetric reduction) of the foam (without extruding sideways) truly allows the seal 512 to compressibly deform to match exactly the contours of the face around the nose. The energy absorptive properties of the foam allow the compressive forces to dissipate and spread somewhat evenly throughout the foam, such that areas requiring more compression (e.g., due to a high point in the facial anatomy) do not require elevated pressure to be exerted at that location. The same approximate pressure is exerted on the skin regardless of a recess or a protrusion in the anatomy.

Figure 26A:
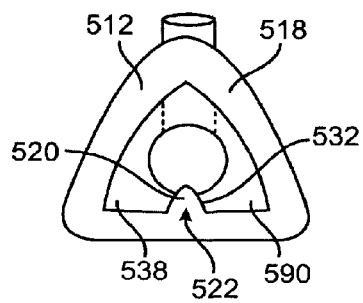
FIGS. 26A-26I show cross-sectional views of a nasal spacer positioned with the nasal mask of FIG. 25.

The foam surface 518 (as shown in FIG. 26A) can optionally be coated, encapsulated or covered (either completely or at certain locations) with a highly compliant elastomeric membrane for the purpose of hygienically controlling contaminants from entering the foam matrix or for facilitating cleaning of the foam surface.

Preferably, the surface pores of the foam at certain areas can be sealed with a compliant sealing substance, or the foam surface can be treated with an antimicrobial coating, or other coatings such as creams or hydrophobic, static, or bacteriostatic coatings or the like.

FIGS. 26A-26I show perspective views of a nasal spacer 520 positioned within the inferior or lower wall 522 of the foam seal 512. The nasal spacer 520 is positioned away from the opening of the nares to prevent nostril occlusion if the mask 500 were to shift during use.

Figure 26B:
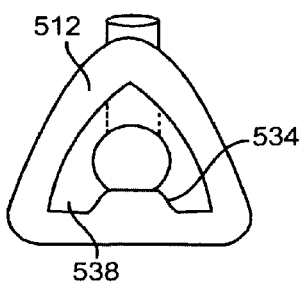
Figure 26C:
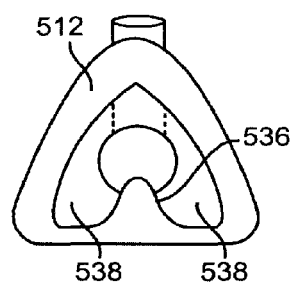
Figure 26D:
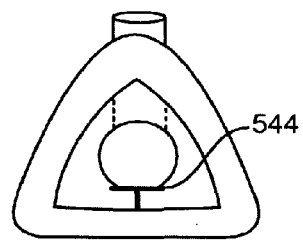
Figure 26E:
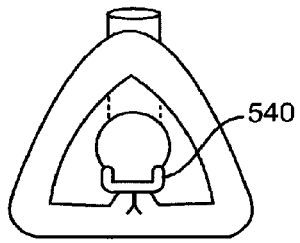
Figure 26F:
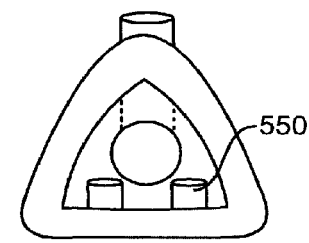
Figure 26G:
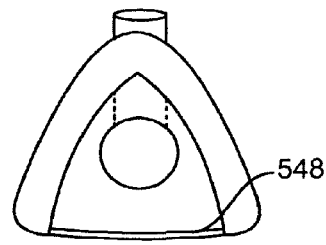
Figure 26H:
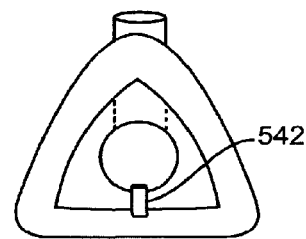
Figure 26I:
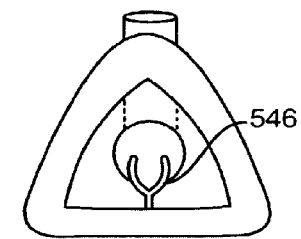
Figure 27A:
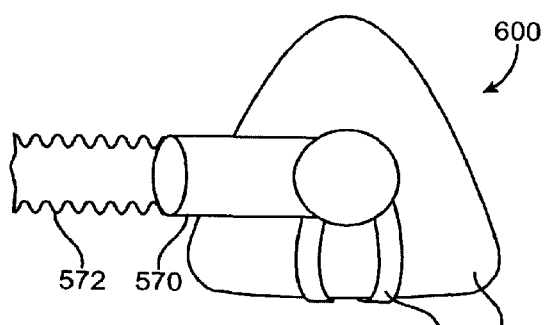
FIG. 27A shows a front view of a hybrid ventilation interface device comprising a nasal mask and a pair of interface tubes.
Figure 27B:
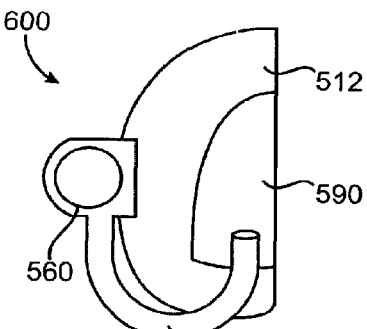
FIG. 27B shows a cross-sectional view of the of the hybrid ventilation interface device of FIG. 27A.
Figure 28A:
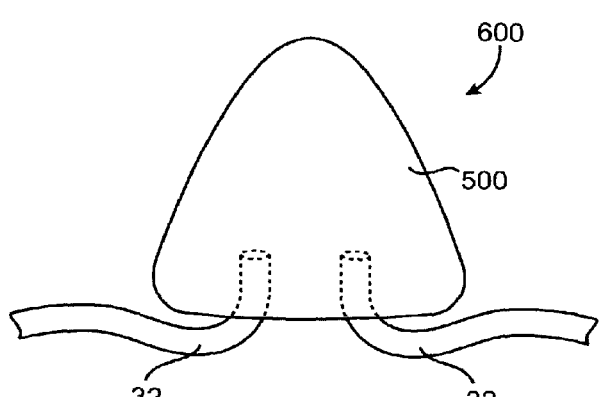
FIG. 28A shows a front view of another embodiment of a hybrid ventilation interface device.
Figure 28B:
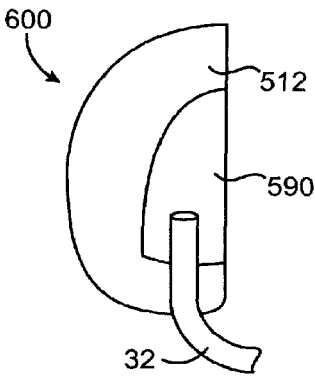
FIG. 28B shows a cross-sectional view of FIG. 28A.
Figure 29A:
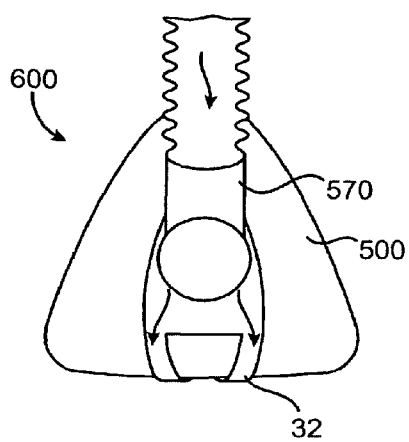
FIG. 29A shows a front view of a further embodiment of a hybrid ventilation interface device.
Figure 29B:
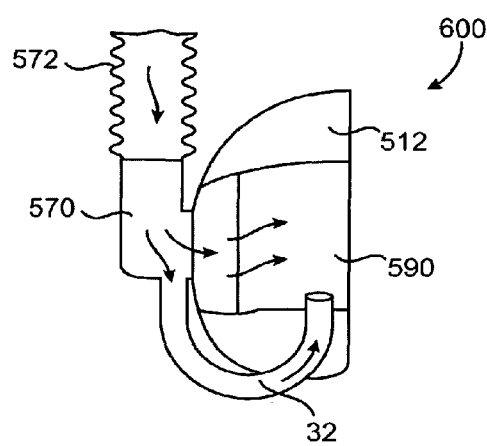
FIG. 29B shows a cross-sectional view of FIG. 29A.

As shown in FIGS. 26A-26I, the nasal spacer 520 can be of a variety of forms, such as (1) a soft compliant Y-shaped or U-shaped prong 530 extending superiorly from the inferior wall for hooking the nostril septum (FIG. 26E); (2) a superiorly extended boss 532, 534, 536 in the medial region of the seal's inferior wall continuous with the seal material (FIGS. 26A, 26B and 26C, respectively); (3) pockets or reliefs 538 in both lateral sides of the seal's inferior wall corresponding to the nostril locations (FIGS. 26A, 26B and 26C); (4) fenestrated 550 (FIG. 26F) or perforated nostril stand-offs 540 (FIG. 26E); (5) a spacer element 542 extending from the mask shell (FIG. 26H); (6) a T-shaped cross bar 544 (FIG. 26G); (7) a spring memory or malleable shapeable nostril septum clip 546 (FIG. 26I); (8) an elastomeric wall 548 defining the inferior seal rather than a foam material (FIG. 26G).

On the convex anterior side of the plastic shell a connector 560 is located, preferably an elbow swivel connector 562, for the purpose of attaching the mask 500 to a tubing 570 connectable to the gas pressure source. Fastening the mask 500 to the face can be performed with conventional strap systems 580 or can be performed with a headband 440 as shown in FIGS. 23A and 23B.

Routing of the breathing circuit tubing can be performed conventionally or can be performed with interconnect tubing 570 (FIG. 25) between the mask 500 and the breathing circuit connector (not shown) which is connected to a neck band.

In an alternative embodiment, a separate vacuum line can be applied to the concave side of the mask shell, thus applying vacuum to that volume when the mask is worn so as to assist in exhalation exhausting, $CO_2$ gas scavenging, enhancing the mask-face seal, or providing active exhalation. The mask's seal area preferably includes an integral exhaust ports extending through the body of the seal 512; the ports may have to be protected from collapse and pinching when the seal is compressed which is preferably accomplished by a pinch-resistant tube extending through the seal width. It can be appreciated that the nasal mask can comprises any, some or all of the described features.

Hybrid Nasal Interface Tubes-Mask Interface

FIGS. 27A, 27B, 28A, 28B, 29A, and 29B show a front and side view, respectively of three (3) ventilation interface devices 600. The devices 600 comprise (1) a mask 500 configured to seal around a portion of the nose including the rim of the nostril or nares; and (2) a pair of nasal interface tubes 32 configured to seal the nostrils. The interface tubes preferably comprise a distal tip 235 configured to seal the nostril. The interface tubes 32 can further include a pair of sealing cushions 46. The hybrid ventilation interface device 600 can be one of the preferred apparatuses or devices for the OSA CPAP user.

As shown in FIGS. 28A, 28B, 29A and 29B, the interface tubes 32 and the mask 500 cavity are both pressurized and are thus both connected to a gas pressure source, either independently or by utilizing the same tubing and connectors. The mask 500 portion can be relatively small compared to conventional masks because there is no worry about the mask edges occluding the nostrils since the nostrils are sealed with the interface tubes 32 hence assuring air delivery into the nose. The mask portion of the assembly secures the nasal interface tubes 32 in place and also provides a seal 510 on the face surrounding the nares.

The seal 512 can be performed with either the nasal interface tubes 32 with a nostril seal or sealing cushions 46, the mask perimeter facial seal 512, or both which can reduce unintended leaks. In this embodiment, when the system 600 is pressurized, the area outside the nares (inside the mask) is pressurized coincident with the inside of the nostrils being pressurized (via the interface tubes), hence there will be an pressure equilibrium between the inside and outside of the nose, thus helping to prevent leaks that occur due to pressurized dilation of the nostrils during CPAP.

In a typical nasal interface system, there is a pressure differential between the nasal cavity 590 (which is elevated positive pressure during CPAP inspiration) and outside the nose (which is ambient pressure) allowing the nostrils to dilate which encourages leakage. In the hybrid system 600, the trans-nasal-wall pressure is equalized.

In a further embodiment, the mask cavity 590 volume can be pressurized during an inspiratory cycle and depressurized during an expiratory cycle, so as to provide easier exhalation effort.

Alternately, the mask cavity 590 volume can be attached to a constant or semi-constant vacuum signal so as to help remove $CO_2$ build up in the overall system 600 or to synchronized to reduce exhalation effort. Alternately, a lower constant pressure level can be applied to the mask cavity 590 volume and a higher constant pressure level applied to the nasal interface tubes 32 with the intention that the interface tubes 32 will seal in the nostrils during inspiration but not exhalation (for example by nasal prong cuff inflation during the inspiratory cycle) thus allowing gas to escape easier during exhalation.

Alternatively only one nostril can be cannulated and/or sealed with a sealing cushion 46 from an interface tubes 32 with a NIT which is substantially sealed in the nostril and through this cannula or tube 32, the nasal cavity is pressurized to the therapeutic pressure level (preferably constantly but optionally intermittently) while the mask's cavity 590 outside the nares is pressurized to a lower exhalation pressure, thus facilitating and easing the work of exhalation out of the non-cannulated nostril. In this embodiment, it can be appreciated that there are a range of combinations, such as cycling pressure in the mask cavity 590 synchronously with the breathing cycle such that during inspiration the open nostril receives positive pressure gas from the mask cavity 590 to prevent flow escapage, but during exhalation the open nostril can receive lower pressure or even negative pressure to encourage exhalation flow.

Alternatively, the side of the nose being cannulated, sealed with a sealing cushion 46 and/or used to delivery inspired flow can be alternated throughout the night, for instance in response to nasal resistance shifting from one side to the other. In other aspects of this hybrid mask 600 embodiment, the mask 500 portion of the interface is not pressurized at all. In these embodiments, the mask shell 510 and/or the interface tubes 32 includes the requisite exhalation exhaust vent fenestrations as is common with conventional interfaces, or can include some or all of the unique exhalation exhaust mechanisms described elsewhere in this disclosure. It can be appreciated that the hybrid interface tubes/mask 600 can include any, some or all of the described features as set forth herein.

Ventilation Interface Head Fasteners

FIGS. 3, 19A and 19B show a method and device for fastening or securing a ventilation interface device 30 to a user's face in a manner comfortable to the user and convenient to wear and remove. The fastening is accomplished with two general methods: (1) with straps 74, 78 that have integral malleable shapeable members 75 that can be shaped by the user and re-shaped repeatedly, or (2) straps 74, 78 that possess spring behavior or shape memory. FIGS. 19A and 19B show a shapeable fastener or strap comprising a malleable member 75. Once shaped into a desired shape, the material within the fastener or strap 74, 78 posses enough strength and deformation resistance to resist inadvertent shape changes.

The malleable fastener assembly can possess several different configurations for attaching to the head. As shown in FIGS. 19A and 19B, the fastener or strap assembly 74, 78 can be two bilateral extensions extending posteriorly from the ventilation interface device 30 wherein the user shapes the extensions to intimately contact the head as desired.

Alternatively, as shown in FIGS. 19A and 19B, the fasteners or straps 74, 78 can be bilateral extensions as already described however with straps attached at their posterior ends wherein the straps can be joined and cinched together at the rear of the head to secure the assembly in place. The fastener or strap 74, 78 can be an upward extension from the interface device 30 extending over the top of the head and down the back of the head toward the neck. In this configuration, the portion at the front of the head (between the eyes) may be very flat and low profile to the skin allowing the user to wear eyeglasses over the fastener.

The fastener or strap 74, 78 can comprise a quick connect feature on at least one end for quick and easy fastening to the interface device at or near the nose and/or at the back of the head, ears or neck band (described in subsequent sections).

Alternatively, the fastener or strap 74, 78 can be fixed to the interface device at one end and attachable at the other end, or a fastener can be fixed to the interface device 30 at one end fastened to something else (neckband, ear, or another fastener) at the opposite end.

The fastener or straps 74, 78 are preferably comprised of the malleable material preferably surrounded, encased, laminated or otherwise covered with a soft compliant material. The malleable material can be copper, nickel, brass or any other suitable material. The cross section of the fastener can be a wire or a plurality of wires, a strip with a flat rectangular cross section, or a round or oval cross section.

The outer covering is preferably a plastic (e.g., soft vinyl), an elastomer (e.g., rubber, synthetic rubber, silicone, and urethane), and a cushion type material (viscoelastic foam). The cushion aspects of the malleable material covering provide comfort and wear-ability of the fastener for the user. The malleable material and the covering can be joined at their interface to make the materials inseparable and behave in unison or can be loosely associated at their interface to allow relative motion between the two materials.

Another embodiment described in FIGS. 19A and 19B is a configuration wherein the malleable member is integral to the interface tubes 32, thus creating giving the interface tubes 32 the added function of a fastener or strap 74, 78.

Another embodiment of the interface fastener or strap 74, 78 is a configuration comprised of both the malleable member and an elastic strip wherein the malleable member is loosely attached to an elastic strip such that the elastic provides stretching and elastic tensioning of the fastener, but at the same time the malleable member provides rigidity of the fastener so it stays in the desired position and shape. The member or members can be attached to the elastic band for example by being sewn into or onto the elastic band, or can be attached to an elastic band by several fabric loops through which the strip is placed.

FIGS. 19A and 19B show one of the preferable embodiments of the spring memory fastener or strap 74, 78. As shown in FIGS. 19A and 19B, the fastener or strap 74, 78 comprises the same types of extension configurations, connections and padding as previously described. It can be appreciated that the fasteners or straps 74, 78 preferably incorporate mixture of features disclosed above can combine flexibility, softness, rigidity where needed, and shapeability.

Ventilation Interface Tubing Securement

FIGS. 3, 19A and 19B also show a method and device for routing and securing the gas delivery tubing for the ventilation interface device 30 in a manner that reduces the obtrusiveness and inconvenience to the conscious user. Specifically, the fastening method and device comprises (1) a second strap 78 in the form of a neckband that is attached to the neck and made of a soft compliant and optionally stretchable material, and easily fastenable onto the neck such as with Velcro, (2) an interconnect connector or bifurcation device 61 comprising a T, Y, and/or elbow swivel connector at the anterior aspect of the neck (e.g., attached to the neckband) with a machine end port and a patient end port, and (3) an interconnect tubing or supply gas hose 64 that connects the ventilation interface device 30, nasal mask 500, or hybrid system 600 to the patient end of the interconnect connector or bifurcation device 61. Tubing leading to the gas pressure source is attached to the machine end of the interconnect connector.

The interconnect connector or bifurcation device 61 is fixed to the second strap 78 or neckband and a second connector 60 (usually an elbow double swivel connector 60, 62) is attachable to the neckband interconnect connector. The interconnect tubes 32 are routed away from the interface device 30 (nose or mouth) to the second strap 78 or neckband in a variety of orientations: (1) either to the rear of the head or neck and then routed along the neck band to the anteriorly located interconnect connector, or (2) to the side of the neck where it is fastened to the neck band and then routed to the interconnect connector, or (3) routed downward from the interface directly to the interconnect connector on the front of the neck band, or (4) routed upward from the interface over the top of the head and down the back of the head to the rear of the neck band, then routed along the neck band to the located interconnect connector.

Figure 32:
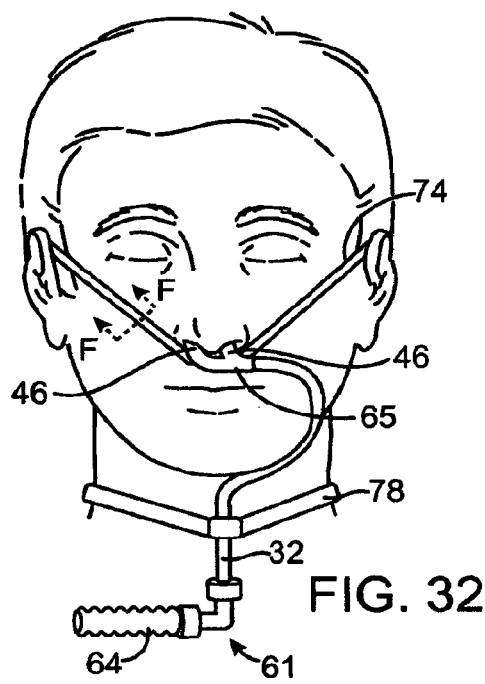
FIG. 32 shows a front view of an alternative embodiment of the nasal interface device.

The interconnect tubing can be two symmetric tubes on either side of the face, head and/or neck as shown in FIG. 3, or can be a single tube as shown in FIG. 32. The section of the interconnect tubing fastened to the second strap 78 can be two symmetric sections of the interface tubes 32, or can be a single tube on one side of the neck as shown in FIG. 32.

In an optional embodiment, the tubing can itself perform the function of a neckband eliminating the need for a separate strap or neckband. A section of the interconnect tubing is preferably a flexible and stretchable (such as a corrugated-walled or ridged tube) to allow kink-resistant flexion in response to head and neck movement such that the interconnect tubing is not inadvertently disconnected on either end. Part of the interconnect tubing can be fastened to the neckband to help secure it in place. Alternatively, the padding can surround part of the interconnect tubing especially if the interconnect tubing is routed to the back of the head or neck or the face to make it comfortable to the user.

It can be appreciated that the tubing routing and fastening systems serve to control the position of tubing so as to direct it away from, for example, the patient's senses (nose, mouth, eyes or ears) in a desirable orientation that is less obtrusive. The tubing can thus be directed away from the users senses or field of vision, thus allowing for more freedom of activities, making it easier to move, and also minimizing the sensation of having one's face tethered to the gas source with a large tube.

In addition to the neckband interconnect arrangements just described, other optional tubing securement and routing systems can be used to accomplish the same objective. For example one alternative configuration is an interconnect connector attached to the lapel area or chest area of a user's night shirt, for example with a grasping clip, or ear lobe clips, thus accomplishing the same objective but without the need for a neck band.

Ventilation Exhaust and Venting

FIGS. 21A, 21B and 21C show an exhalation flow and $CO_2$ blow-off exhaust ports device. As discussed, exhaust ports 370 are preferably a requirement in conventional OSA CPAP interfaces (nasal masks and nasal interface tubes) whereas they are not required in non-CPAP ventilation because non-CPAP ventilation systems include a separate exhalation valve in the system. In the present invention, five different types of exhaust systems are disclosed; (1) angulated fenestrations axially angulated in the direction of exhaled flow, (2) an exhaust intake scoop, (3) a directional flapper valve, (4) a directional sleeve valve, and (5) a vacuum assisted exhaust port.

FIGS. 21A and 21B show angulated fenestrations, which are placed in the wall of the nasal interface tubes 32 at or near the base of the sealing cushions 46 (i.e., located outside of the nostrils below the nose). The fenestrations or vent ports 370 are preferably placed at a diagonal angle 380 so as to direct the air in a downward (inferior) and outward (forward or anterior) direction 382 so that the exhaust flow direction simulates that of air normally being exhaled from the nose. This minimizes annoyance to the user and bed partner. The angulated fenestrations or vent ports 370 have the added benefit of biasing the degree of flow resistance such that resistance is low when flow inside the interface tubes 32 is in the exhaled direction and high when flow inside the interface tubes is in the inhaled direction, because the entrance of to the channels from inside the interface tubes are generally parallel with the direction of exhaled flow, but at 180° angles to the direction of inspired flow. Thus, the angulated fenestrations or vent ports 370 increase the exhaust leak in the "vacuum assisted exhaust systems."

The vacuum exhaust is preferably created by a separate vacuum line with a distal end communicating with the lumen of the breathing circuit tube at a location somewhat at or near the patient interface (nasal mask or nasal interface tubes) and a proximal end connected to a vacuum generating source. A constant or intermittent vacuum is applied to remove CO rich gas. Preferably, the vacuum can be created by a retrograde (reverse direction) positive pressure jet airflow, which will entrain air to escape with it (i.e., a venturi effect). However, the exhaust system vacuum can be constant, intermittent and/or timed with the breathing cycle (e.g., on during exhalation phase and off during inspiration phase). In the venturi system, the venturi pressure source and the ventilation gas pressure source can be the same source or different sources.

Portable PGU 700

Figure 30:
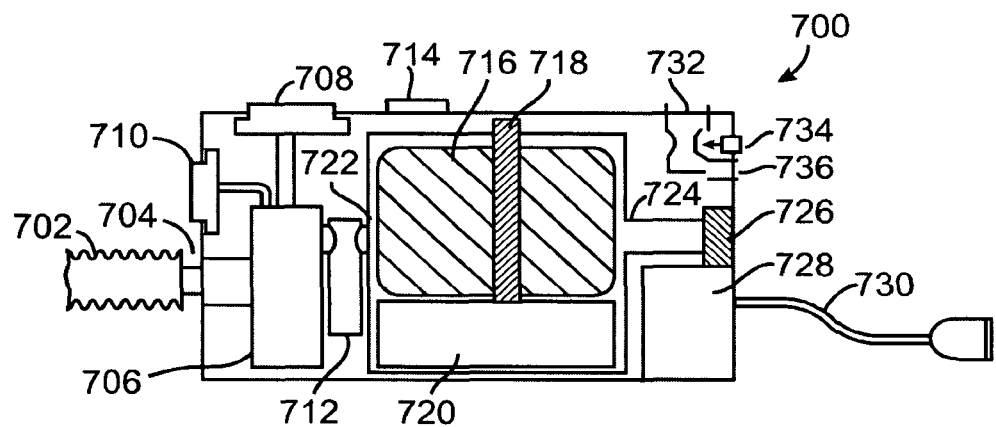
FIG. 30 shows a front view of a portable breathing gas pressure generating and delivery unit.
Figure 31:
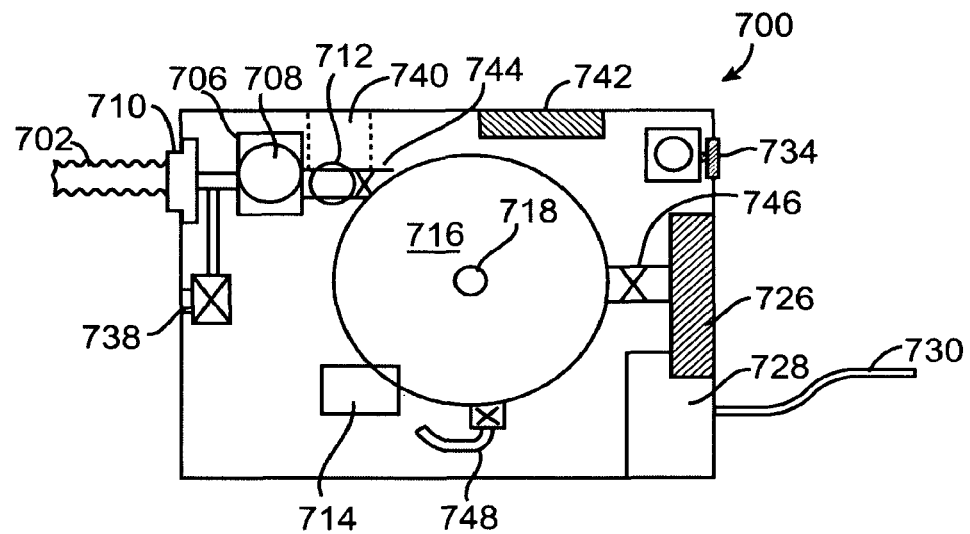
FIG. 31 shows a top view of the portable breathing gas pressure generating and delivery unit of FIG. 30.

FIGS. 30 and 31 shows a portable breathing gas pressure generating and delivery unit 700 (PGU), which is designed to be compact and portable for travel purposes.

Typically, the conventional PGU's for CPAP and BiPAP applications have a variable speed motor to control a variable speed air blower fan (ABF) and the requisite digital electronics and microprocessors, analog electronics, sensors and software to control the speed of the motor. The user sets the prescribed therapeutic pressure level and the ABF speed is automatically adjusted as necessary compensating for the prevailing conditions (tubing resistance, etc.) to achieve that pressure.

In the present invention the ABF is not automatically adjusted and instead the user sets the speed of the motor/ABF manually until the desired pressure output is achieved. The motor control electronics can thus be made less inexpensive and possibly smaller for more compactness.

As shown in FIGS. 30 and 31, the portable breathing gas pressure generating and delivery unit comprises a gas supply hose 702, a gas outlet tubing connector 704, a pressure regulator 706, a regulator adjustment 708, a pressure gauge 710, a moisture trap 712, a motor and fan speed selector switch 714, a fan and blower 716, a fan and blower shaft 718, a fan and blower motor 720, a fan and blower gas outlet 722, a fan and blower gas inlet 724, replaceable HEPA filter 726, a power supply module 728 comprising a rechargeable battery, transformer, fuse and other related components, a power cord 730 for either AC or 12V DC current; an adjustable airway resistance simulator and breathing circuit 734 configured such that the user can adjust the pressure output; an airway resistance simulator adjustment device 736 configured to allow the user to adjust selected high and low resistance, a airway resistance gas outlet 738, an exhalation exhaust flapper valve 740, an access compartment for accessing the moisture trap 742, a filter, air inlet and outlet 744 configured to cool the device, a blower fan outlet check valve 746, a blower fan inlet check valve 748, a blower fan bleed to cool the inside of the unit including the motor or blower fan and/or auxiliary inlet to obtain warm air from the motor heat into the blower and thus entraining into a gas delivered to the use to warm the gas 750, a rubberized surface 752 and a sliding door to protect the controls and connections 754.

In a second embodiment of the portable PGU 700, a new manner of calibrating the pressure output of the PGU 700 to the individual user is described. To facilitate proper pressure output setting, the PGU 700 includes an airway resistance simulator test port 756. The user attaches the distal end of the breathing circuit tube or gas supply hose 702 to the test port 756 while setting the pressure setting. The resistance simulator has several settings to properly simulate the resistance of the individual's airway or the degree of their airway obstruction. For example, if the individual has a very high critical opening pressure of their airway, they would set the simulator setting to maximum and in contrast an individual with a low critical opening pressure of their airway would set the simulator setting to minimum. The simulator settings would be for example 1-5, 5 being highest. This way the pressure output is set with the correct resistance in place.

In a third embodiment of the portable PGU 700, optional pressure generating mechanisms are described. Besides the conventional rotary vane blower and fan 716 for generating pressure, the pressure can be generated by (1) a fan with a concentric motor, (2) a piston pump, (3) a turbine, (4) a centrifugal pump, (5) a gear pump, (6) a rotary piston pump, (7) an impeller pump, or (8) an dual action piston pump with the same direction output on both strokes by the use of valves. Also, besides generating flow with the conventional single pump systems, there can be an array of small pumps, preferably in parallel, so as to create greater flow output in a smaller overall size, or to alternate between pumps where the pump outputs are non-continuous as in a piston pump.

In a forth embodiment of the portable PGU 700 to further facilitate portability, the unit can be powered with a non-120 Volt AC power source, such as a 12 Volt DC power source (with an internal battery, an external battery or cigarette lighter power cord) and is equipped accordingly. Additionally the unit 700 can be equipped with a charging system, for example a chargeable power storage device (e.g., battery, capacitor) connectable to a power source such as a transformer and/or 120/240 Volt AC supply and/or DC supply. The charging system input power can be attached with a simple conventional connector or can be a docking station. Or the chargeable power storage unit can be modular and replaceable into the PGU 700 and charged outside of the unit 700. Further, the charging of the power storage unit can be a manually charging system, such as a manual wind-up system.

In a fifth embodiment of the portable PGU 700, the air being delivered to the patient can be conditioned in a variety of manners, such as moisturizing and warming. Warming can be accomplished by collecting warm air that is generated from the ABF or pump motor and inputting it into the ABF, or by channeling the ABF air output past the motor to warm the air. Moisturization can be accomplished by including a low resistance filter in the ABF air outlet path wherein the filter can be wetted by the user so that the air collects moisture on the way to the patient. Further, the moisturizer can be warmed by warm air that is collected from the ABF motor, or alternately can be warmed by a peltier element. In these embodiments the ABF motor is also prevented from overheating do to the bleeding off of heat.

In a sixth embodiment of the portable PGU 700, the unit 700 may also include an exhalation valve (for example a directional flapper valve) that leaks to atmosphere during exhalation but which is sealed to atmosphere during inspiration. The valve is preferably included near the air outlet of the PGU 700.

In a further embodiment of the portable PGU 700, the unit is constructed with flush mounted, recessed mounted or cover-protected dials, gauges, connectors and controls to avoid damage to it. This facilitates reliability and robustness of the unit for traveling use.

In another embodiment of the portable PGU 700, the unit enclosure is ruggedized, for example by using polymer or rubber construction of the enclosure, or by surrounding the enclosure with rubber or polymer protection. The PGU 700 can also include a corrugated air hose that can be compressed from its full length of 6'-8' to 1' to facilitate portability. The PGU 700 can also bleed off room temperature air in the ABF to cool the inside of the PGU 700 to prevent overheating. The PGU 700 can be super-insulated for noise dissipation and abatement.

It can be appreciated that the PGU 700 comprises all the requisite regulators, valves, sensors, gauges, conduits, electric wiring, analog and digital electronics. The purpose of these novel features is to provide a portable PGU 700 that is extremely low cost and small footprint such that travelers can easily travel with the equipment and perhaps own a dedicated travel PGU 700 rather than traveling with their heavier more expensive PGU 700. A typical user would be a frequent traveler such as a sales representative, persons taking overseas flights frequently, or a truck driver who can keep the PGU 700 in the truck and use it with 12 VDC. It should be noted that any and all of these embodiments can be combined or mixed as needed.

It can be appreciated that while the various embodiments described are especially useful for OSA CPAP applications, they are also useful for other non-OSA and non-CPAP applications such as emergency, NIV, COPD, weaning from IMV, or the like.

Alternative Aspects of the Nasal Interface Device

FIG. 32 shows a front view of an alternative embodiment of the nasal interface device 30. As shown in FIG. 32, the device comprises a gas supply hose 64, a hose coupler 60, a tube 32A and a bifurcated nasal cushion 64A. The nasal cushion 65 comprises a first end configured to attach to the tube 32 and a second end configured to receive a pair of sealing cushions 64. Alternatively, the second end of the nasal cushion can be designed with the sealing cushions 64 fixed to the second end of the nasal cushion 65.

The nasal cushion 65 is preferably designed to avoid the turbulent flow associated with the base manifold 20 as shown in FIGS. 1 and 2 by incorporating gradual curves or arcuate design into the nasal cushion 65. Preferably, the nasal cushion 65 comprises a pair of lumens 69 configured to deliver a ventilation gas to the nostril of the user. The lumens 69 preferably do not have any 90 degree angles and provide a smooth and arcuate configuration for laminar flow.

The device 30 is secured to the user with a first strap 74 (headband) and a second strap 78 (neckband). As shown in FIG. 32, the device 30 is secured to the neck and then is positioned on or around the jaw of the user. It can be appreciated that the device 30 can be positioned on or around the jaw of the user from either side (FIGS. 32 and 33A) of the face to allow the wear to sleep more comfortably on one side or the other. Alternatively, the tube 32 can be an over the head tube configuration secured to the user by known methods of over the head style nasal interface cannulae and devices as shown in FIG. 33B.

Figure 34:
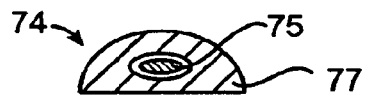
FIG. 34 shows a cross sectional view of a strap of FIG. 32 along line F-F.

FIG. 34 shows a cross-section of a first strap 74 or a second strap 78 taken along the line F-F of FIG. 32. As shown in FIG. 34, the first strap 74 or second strap 78 comprises a malleable material 75 preferably surrounded, encased, laminated or otherwise covered with an outer material 77 of a soft compliant nature. The malleable material 75 can be copper, nickel, brass or any other suitable material. Alternatively, the malleable material 75 as shown in FIG. 34 can be a wire or a plurality of wires, a strip with a flat rectangular cross section, or a round or oval cross section.

The outer material 77 is preferably comprises of a plastic (e.g., soft vinyl), an elastomer (e.g., rubber, synthetic rubber, silicone, and urethane), or a cushion type material (viscoelastic foam). The cushion aspects of the outer material 77 provide comfort and wearability of the straps 74, 78 for the user. The malleable material 75 and the outer material 77 can be joined at their interface to make the materials inseparable and behave in unison or can be loosely associated at their interface to allow relative motion between the two materials.

The first strap 74 and the second strap 78 are preferably fastened behind the head and/or neck by a Velcro system 174, 178, respectively. However, it can be appreciated that other methods of connecting the ends of the straps 74, 78 can be implemented without departing from the invention.

Figure 33A:
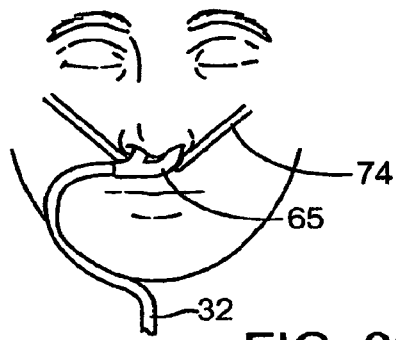
FIG. 33A show a front view of a further embodiment of the nasal interface device of FIG. 32.
Figure 33B:
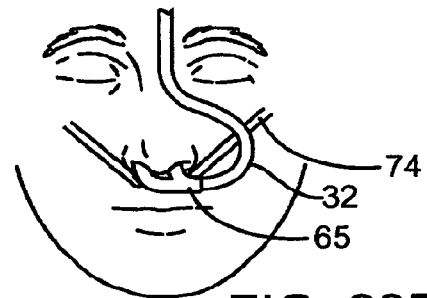
FIG. 33B shows a front view of another embodiment of the nasal interface device of FIG. 32.
Figure 35:
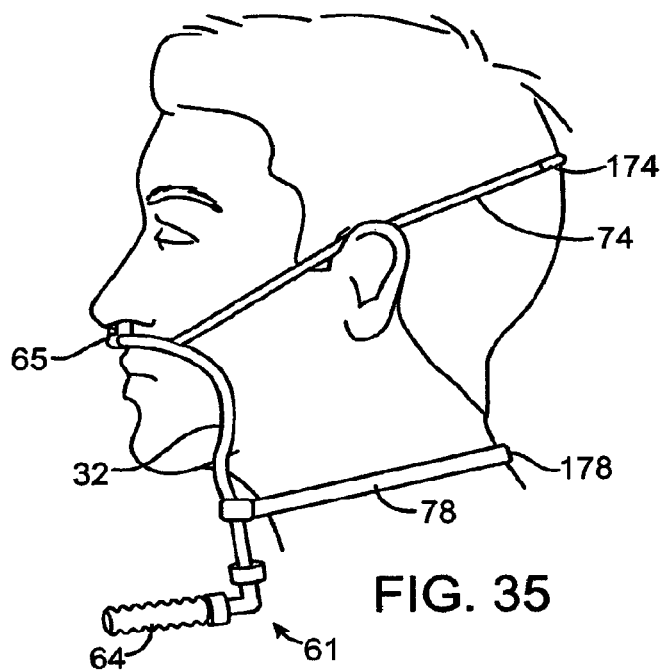
FIG. 35 shows a side view of the nasal device of FIG. 32 showing how the device hugs the face for comfort.

FIG. 35 shows a side view of the nasal interface device of FIGS. 32, 33A and 33B. As shown in FIG. 35, the device 30 is designed to fit closely and hug the face of the user. The close fit and hugging nature of the device 30 provides for as much comfort as possible.

It can be appreciated that the tubes 32 can also include a shape memory material. The shape memory material is created by a preformed shape or by a shape memory member which is integral to at least a portion of the tubing.

The nasal device as shown in FIGS. 3A and 4 have been tested for both air flow resistance and estimated noise production. Table 1 is a sample of those test results.

TABLE 1

Air Flow Resistance (cm H₂0 vs. LPM)

|  | 30 | 50 | 80 |
|---|---|---|---|
| Conventional Device #1 | | | |
| XS (size) | 0.5 | 1.3 | 3.1 |
| S | 0.5 | 1.1 | 2.6 |
| L | 0.4 | 1.0 | 2.0 |
| XL | 0.4 | 1.0 | 1.8 |
| Conventional Device #2 | | | |
| X (size) | 0.2 | 0.5 | 1.3 |
| S | 0.2 | 0.5 | 1.1 |
| M | 0.2 | 0.5 | 1.1 |
| X | 0.2 | 0.5 | 1.1 |
| Conventional Device #3 | | | |
|  | 0.2 | 0.4 | 1.0 |
| Nasal Device as Shown in FIGS. 3A and 4 | | | |
| S (size) | 0.2 | 0.3 | 0.9 |

Noise Production (db's at 50 LPM - estimated at a 2 to 3 foot distance from the device)

| Device #1 | 45.0 |
|---|---|
| Device #2 | 50.0 |
| Device #3 | not available |
| Nasal Device | 42.0 |

As shown by the test results in Table 1, the nasal interface device 30 as shown in FIGS. 3A and 4 provides for reduced air flow resistance as a result of the laminar flow of the device which delivers the ventilation gas without turbulent flow as known in the prior art. Furthermore, the reduced air flow resistance provides reduced noise production.

Figure 36A:
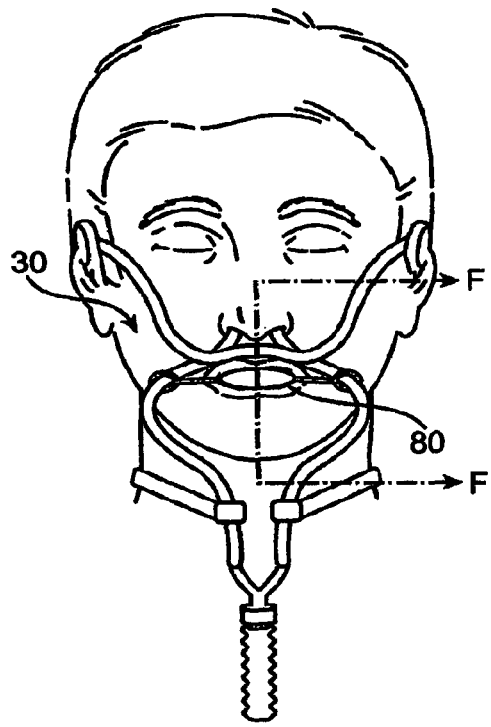
FIG. 36A shows a front view of a mouth guard according to one embodiment of the present invention.
Figure 36B:
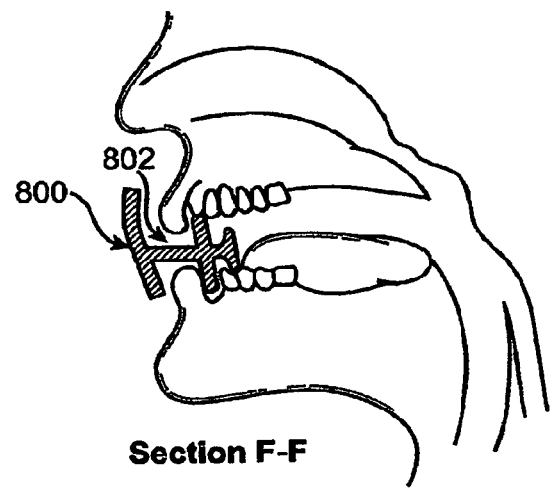
FIG. 36B shows a cross-sectional view of the mouth guard of FIG. 36A along the line F-F.

FIGS. 36A and 36B describe an alternate embodiment that includes a mouth shield 80, 800 that helps prevent leakage of ventilation gas out of the mouth in the event the user is a mouth breather. The shield is a highly compliant structure that fits between the lips and teeth and on the outside of the mouth shield can be attached to the cannula tubing. The shield can include a posterior protrusion 802 that extends behind the front teeth to facilitate retention in the mouth.

Figure 37:
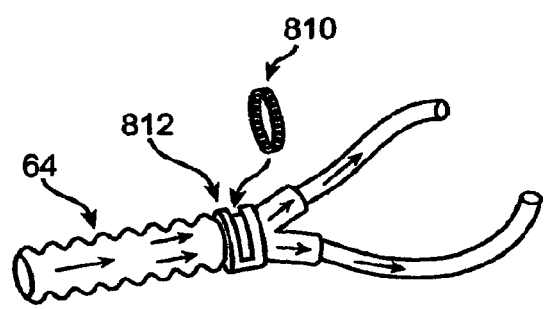
FIG. 37 shows a perspective view of an aromatherapy delivery technique.

FIG. 37 describes an optional embodiment in which aroma therapy is provided to calm a user (or other therapeutic uses) by means of a reservoir or cartridge release system 810 that releases aroma molecules inline 812 into the ventilation gas supply. Optionally, the aroma therapy can be provided by simply applying the solution to the cannula apparatus, for example, while washing.

While the invention has been described in detail with reference to the preferred embodiments thereof, it will be apparent to one skilled in the art that various changes and modifications can be made and equivalents employed, without departing from the present invention.

The invention claimed is:

1. A nasal ventilation interface for the purpose of supplying ventilation gas to a person's airway, the interface comprising:
    a generally tubular construction with a distal end configured with a first and a second tube for engagement with a person's nostrils and each defining an angulated fenestration in alignment with and directly opposed to a nostril opening, the angulated fenestration being diagonally oriented with respect to a person's face to define a nostril airflow direction outward from the face and downward from the nostril, a proximal end configured for attachment to a ventilation gas supply hose;
    a coupler connecting the first and second distal ends of the tubes; and
    a lifting device applied substantially directly under the nose to the distal end of the first and second tubes, wherein the lift creates and maintains an upward engagement force between the respective first and second distal ends of the tubes and the nostrils, and maintains the angulated fenestration oriented along the nostril airflow direction.

2. The interface of claim 1, wherein the lifting device is a first strap attachable to the distal end of the tubes via the coupler.

3. The interface of claim 2, wherein the first strap comprises two ends, wherein the two ends extend bilaterally away from the nose and join at the back or side of the head.

4. The interface of claim 2, wherein the first strap further comprises a malleable member.

5. The interface of claim 2, wherein the first strap further comprises a shape memory member.

6. The interface of claim 2, wherein the tension and location of the first strap are adjustable.

7. The interface of claim 2, further comprising a facial pad, wherein the facial pad is attachable to the first strap and positions the distal end of the interface beneath the nose.

8. A nasal ventilation interface apparatus for the purpose of supplying ventilation gas to a person's airway, the apparatus comprising: a generally tubular construction with a distal end comprising a first and second tube configured to engage a person's nostrils and each defining an angulated fenestration in alignment with and directly opposed to a nostril opening, the angulated fenestration being diagonally oriented with respect to a person's face to define a nostril airflow direction outward from the face and downward from the nostril, and a proximal end configured to attach to a ventilation gas supply hose, wherein the distal end comprises a facial pad positioned between the tubes and skin between the user's nose and upper lip, and wherein the facial pad cushions the user's shin and tilts the distal end of the tubes to maintain the angulated fenestration oriented along the nostril airflow direction and align each of the first tube and the second tube with a rim of the user's nostrils.

9. The apparatus of claim 8, wherein the facial pad is comprised of a viscoelastic material and the pair of tubes are comprised of a plastic material.

10. The apparatus of claim 8, wherein the facial pad is comprised of an energy absorption material.

11. The apparatus of claim 8, wherein the facial pad is adjustable or a variety of facial pad sizes can be interchanged.

12. The apparatus of claim 8, wherein the facial pad is integral to a coupler, a head strap connector, the first and second tubes, or sealing cushions.

13. The apparatus of claim 8, wherein the facial pad is attached to a head strap connector with a hinge.

14. A nasal ventilation interface apparatus for the purpose of supplying ventilation gas to a person's airway comprising:
    a generally tubular construction with a distal end comprising a first and a second tube configured to engage a person's nostrils and each defining an angulated fenestration in alignment with and directly opposed to a nostril opening, the angulated fenestration being diagonally oriented with respect to a person's face to define a nostril airflow direction outward from the face and downward from the nostril, and a proximal end configured to attach to a ventilation gas supply hose, a band member substantially circumventing the head from the chin to the top of the head, wherein the band member applies upward compression on the chin so as to bias the mouth in a close state, and a first connector between the first tube and the band member and a second connector between the second tube and the band member, wherein the first connector and the second connector apply an upward lifting force on distal ends of the first tube and the second tube to maintain a seal with the nostrils, and maintain the angulated fenestration oriented along the nostril airflow direction.

15. The apparatus of claim 14, wherein the hand member provides an upward force on the distal end first and second tubes, wherein the force maintains compression between the nostrils and the distal ends of the first and second tubes wherein the compression substantially seals the first and second tubes to the nostrils.

16. The apparatus of claim 14, wherein the distal end of the tubes is generally circular and comprises an inner diameter generally approximately equal to or less than the diameter of the nostril opening of the user.

17. The apparatus of claim 16, wherein the distal end of the tubes has an inner diameter of about 6 mm to about 22 mm.

* * * * *